United States Patent [19]
Grieninger et al.

[11] Patent Number: 6,025,476
[45] Date of Patent: Feb. 15, 2000

[54] MONOSPECIFIC ANTIBODIES AGAINST A SUBUNIT OF FIBRINOGEN

[75] Inventors: Gerd Grieninger; Yiping Fu, both of New York; Yan Cao, Valhalla, all of N.Y.; Mohamad Zaher Ahadi, Paterson; Bohdan J. Kudryk, Hillsdale, both of N.J.

[73] Assignee: New York Blood Center, Inc., New York, N.Y.

[21] Appl. No.: 09/167,647

[22] Filed: Oct. 6, 1998

Related U.S. Application Data

[62] Division of application No. 08/479,755, Jun. 7, 1995, Pat. No. 5,817,768.

[51] Int. Cl.⁷ ..................................... C07K 16/00
[52] U.S. Cl. ..................... 530/388.1; 424/94.67; 435/7.92
[58] Field of Search ....................... 530/388.1; 424/94.67

[56] References Cited

U.S. PATENT DOCUMENTS

| | | | |
|---|---|---|---|
| 5,817,768 | 10/1998 | Grieninger et al. | 530/388.1 |
| 5,830,468 | 11/1998 | Bini | 424/94.67 |

OTHER PUBLICATIONS

Blomback B, "Fibrinogen and fibrin formation and its role in fibrinolysis", in Goldstein J, ed., *Biotechnology of Blood*, 225–279 (1991).

Bini A, and Kudryk BJ, "Fibrin and its derivatives in the normal and diseased vessel wall", *Ann. N.Y. Acad. Sci.* 667:112–126 (1992).

Dvorak HF, Nagy JA, Berse B, Brown LF, Yeo K–T, Yeo T–K, Dvorak AM, Van de Water L, Sioussat TM, and Senger DR, "Vascular Permeability factor, fibrin, and the pathogenesis of tumor stroma formation", *Ann N.Y. Acad. Sci.* 667:101–111 (1992).

Fu Y, Weissbach L, Plant PW, Oddoux C, Cao Y, Liang TH, Roy SN, Redman CM, and Grieninger G, "Carboxy–terminal–extended variant of the human fibrinogen α subunit: a novel exon conferring marked homology to β and γ subunits", *Biochemistry* 31:11968–11972 (1992).

Blomback B, Blomback M, Henschen A, Hessel B, Iwanaga S, and Woods KR, "N–terminal disulphide knot of human fibrinogen", *Nature* 218: 130–134 (1968).

Lottspeich F, and Henschen A, "Amino acid sequence of human fibrin. Preliminary note on the completion of the gamma–chain sequence", *Hoppe–Seyler's Z. Physiol. Chem.* 358:935–938 (1977).

Henschen A, and Lottspeich F, "Amino Acid sequence of human fibrin, preliminary note on the completion of the beta–chain sequence", *Hoppe–Seyler's Z. Physiol. Chem.* 358:1643–1646 (1977).

(List continued on next page.)

*Primary Examiner*—James C. Housel
*Assistant Examiner*—Ginny Allen Portner
*Attorney, Agent, or Firm*—Hoffman & Baron, LLP

[57] ABSTRACT

The invention provides monospecific antibodies which are specifically reactive with the $\alpha_E$ subunit of fibrinogen or a fragment thereof, but not with other portions of the fibrinogen molecule. The invention also provides anti-$\alpha_E$ probes, including monospecific anti-$\alpha_E$ antibodies which have been detectably labeled. In addition, the invention provides methods of using the monospecific antibodies for detection of the $\alpha_E$ subunit and fragments thereof, as well as reagents and kits for performing the methods. Diagnostic methods for determining information associated with atherogenesis and/or thrombogenesis, as well as for determining information associated with pregnancy status or outcome. The invention further provides continuous cell lines which produce monospecific anti-$\alpha_E$ antibodies.

9 Claims, 8 Drawing Sheets

```
                   620              640              660
RAT         ------------A-N---S-------------------------------
MAN         DCDDVLQTHPSGTQSGIFNIKLPGSSKIFSVYCDQETSLGGWLLIQQRMDGSLNFNRTWQ
RABBIT      ------------A---------------------------------------

680              700              720
RAT         -----------K---------------L--------------K------------
MAN         DYKRG FGSLNDEGEGEFWLG NDYLHLLTQRGSVLRVELEDWAGNEAYAEYHFRVGSEAEG
RABBIT      -----------K----------Q-----L-A----------D-RGD-------------

740              760              780
RAT         --------Q-------M-------T-----S-------------------------
MAN         YALQVSSYEGTAGDALIEGSVEEGAEYTSHNNMQFSTFDRDADQWEENCAEVYGGGWWYN
RABBIT      ------------------------------------------H----------------

800              820              840
RAT         S--------------T--------------L--P--------W----------G-
MAN         NCQAANLNGIYYPGGSYDPRNNSPYEIEN GVVWVSFRGADYSLRAVRMKIRPLVTQ
RABBIT      --------------P-----------------P-----------.........
```

OTHER PUBLICATIONS

Henschen A, Lottspeich F, and Hessel B, "Amino acid sequence of human fibrin, preliminary note on the completion of the intermediate part of the alpha–chain sequence", *Hoppe–Seyler's Z. Physiol. Chem.* 360:1951–1956 (1979).

Doolittle RF, Watt KWK, Cottrell BA, Strong DD, and Riley M, "The amino acid sequence of the alpha–chain of human fibrinogen", *Nature* 280:464–468 (1979).

Kant JA, Fornace Jr AJ, Saxe D, Simon MI, McBride OW, and Crabtree GR, "Evolution and organization of the fibrinogen locus on chromosome 4: Gene duplication accompanied by transposition and inversion", *Proc. Natl. Acad. Sci. USA* 82:2344–2348 (1985).

Chung DW, Harris JE, and Davie EW, "Nucleotide sequences of the three genes coding for human fibrinogen", *Adv. Exp. Med. Biol.* 281:39–48 (1991).

Weissbach L, and Grieninger G, "Bipartite mRNA for chicken alpha–fibrinogen potentially encodes an amino acid sequence homologous to beta–and gamma–fibrinogens", *Proc. Natl. Acad. Sci. USA* 87:5198–5202 (1990).

Fu Y, and Grieninger G, "Fib$_{420}$: A normal human variant of fibrinogen with two extended α chains", *Proc. Natl. Acad. Sci. USA* 91:2625–2628 (1994).

Pan Y, and Doolittle RF, "cDNA sequence of a second fibrinogen alpha chain in lamprey: An archetypal version alignable with full–length beta and gamma chains", *Proc. Natl. Acad. Sci. USA* 89:2066–2070 (1992).

Doolittle RF, Riley M, and Pan Y, "Direct measurement of a second fibrinogen alpha chain in lamprey blood plasma", *Thromb. Res.* 68:489–493 (1992).

Chung DW, Que BG, Rixon MW, Mace Jr M, and Davie EW, "Characterization of complementary deoxyribonucleic acid and genomic deoxyribonucleic acid for the beta chain of human fibrinogen", *Biochemistry* 22:3244–3250 (1983).

Chung DW, Chan W–Y, and Davie EW, "Characterization of a complementary deoxyribonucleic acid coding for the gamma chain of human fibrinogen", *Biochemistry* 22:3250–3256 (1983).

Baker NE, Mlodzik M, and Rubin GM, "Spacing differentiation in the developing Drosophila eye: A fibrinogen–related lateral inhibitor encoded by scabrous", *Science* 250:1370–1377 (1990).

Koyama T, Hall LR, Haser WG, Tonegawa S, and Saito H, "Structure of a cytotoxic T–lymphocyte–specific gene shows a strong homology to fibrinogen beta and gamma chains", *Proc. Natl. Acad. Sci. USA* 84:1609–1613 (1987).

Morel Y, Briston J, Gitelman SE, and Miller WL, "Transcript encoded on the opposite strand of the human steroid 21–hydroxylase/complement component C4 gene locus", *Proc. Natl. Acad. Sci. USA* 86:6582–6586 (1989).

Nies DE, Hemesath TJ, Kim J–H, Gulcher JR, and Stefansson K, "The complete cDNA sequence of human hexabreachion (tenascin)", *J. Biol. Chem.* 266:2818–2823 (1991).

Norenberg U, Wille H, Wolff JM, Frank R, and Rathjen FG, "The chicken neural extracellular matrix molecule restrictin: Similarity with EGF–, fibronectin type III–, and fibrinogen––like motifs", *Neuron* 8:849–863 (1992).

Xu X, and Doolittle RF, "Presence of a vertebrate fibrinogen–like sequence in an echinoderm", *Proc. Natl. Acad. Sci. USA* 87:2097–2101 (1990).

Chan AM–L, Rubin JS, Bottaro DP, Hirschfield DW, Chedid M, and Aaronson SA, "Identification of a competitive HGF antagonist encoded by an alternative transcript", *Science* 254:1382–1385 (1991).

Descombes P, and Schibler U, "A liver–enriched transcriptional activator protein, LAP, and a transcriptional inhibitory protein, LIP, are translated from the same mRNA", *Cell* 67:569–579 (1991).

Early P, Rogers J, David M, Calame K, Bond M, Wall R, and Hood L, "Two mRNAs can be produced from a single immunoglobulin mu gene by alternative RNA processing pathways", *Cell* 20:313–319 (1980).

Hynes RO, "Integrins: Versatility, modulation, and signaling in cell adhesion", *Cell* 69:11–25 (1992).

Kloczewiak M, Timmons S, Lukas TJ, and Hawiger J, "Platelet receptor recognition site on human fibrinogen. Synthesis and structure–function relationship of peptides corresponding to the carboxy–terminal segment of the gamma chain", *Biochemistry* 23:1767–1774 (1984).

Cheresh DA, Berliner SA, Vincente V, and Ruggeri ZM, "Recognition of distinct adhesive sites on fibrinogen by related integrins on platelets and endothelial cells", *Cell* 58:945–953 (1989).

Loike JD, Sodeik B, Cao L, Leucona S. Weitz JI, Detmers PA, Wright SD, and Silverstein SC, "CD11c/CD18 on neutrophils recognizes a domain at the N terminus of the A–alpha chain of fibrinogen", *Proc. Natl. Acad. Sci. USA* 88:1044–1048 (1991).

Farrell DH, Thiagarajan P, Chung DW, and Davie EW, "Role of fibrinogen alpha and gamma chain sites in platelet aggregation", *Proc. Natl. Acad. Sci. USA* 89:10729–10732 (1992).

Gonda SR, and Shainoff JR, "Adsorptive endocytosis of fibrin monomer by macrophages: Evidence of a receptor for the amino terminus of the fibrin alpha chain", *Proc. Natl. Acad. Sci. USA* 79:4565–4569 (1982).

Ribes JA, Ni F, Wagner DD, and Francis CW, "Mediation of fibrin–induced release of von Willebrand factor from cultured endothelial cells by the fibrin beta chain", *J. Clin Invest.* 84:435–442 (1989).

Ernst E, "Plasma fibrinogen—An independent cardiovascular risk factor", *J. Internal Med.* 227:365–372 (1990).

Ernst E, and Resch KL, "Fibrinogen as a cardiovascular risk factor: A meta–analysis and review of the literature", *Ann Intern. Med.* 118:956–963 (1993).

Bini A, Fenoglio JJ, Sorbel J, Owen J, Fejgl M, and Kaplan KL, "Immunochemical characterization of fibrinogen, fibrin I, and fibrin II in human thrombi and atherosclerotic lesions", *Blood* 69:1038–1045 (1987).

Valenzuela R, Shainoff JR, DiBello PM, Urbanic DA, Anderson JM, Matsueda GR, and Kudryk BJ, "Immunoelectrophoretic and immunohistochemical characterizations of fibrinogen derivatives in atherosclerotic aortic intimas and vascular prosthesis pseudo–intimas", *Am. J. Pathol.* 141:861–880 (1992).

Felding–Habermann B, Ruggeri ZM, and Cheresh DA, "Distinct biological consequences of integrin alpha–v–beta–3–mediated melanoma cell adhesion to fibrinogen and its plasmic fragments", *J. Biol. Chem.* 267:5070–5077 (1992).

Koopman J, Haverkate F, Grimbergen J, Egbring R, and Lord ST, "Fibrinogen Marburg: A homozygous case of dysfibrinogenemia, lacking amino acids A–alpha 461–610 (Lys 461 AAA—Stop TAA)", *Blood* 80:1972–1979 (1992).

Justus B, Siegert G, and Tiebel O, "Changes of parameters of hemostasis and fibrinolysis during normal pregnancy", *Zent bl Gynäkol* 114:165–70 (1992) (in German).

Kitchens CS, Cruz AC, and Kant JA, "A unique 7p/12q chromosomal abnormality associated with recurrent abortion and hypofibrinogenemia", *Blood* 70:921–25 (1987).

Goodwin TM, "Congenital hypofibrinogenemia in pregnancy", *Obstet Gynecol* 44:157–61 (1989).

Parasnis H, Raje B, and Hinduja IN, "Relevance of plasma fibrinogen estimation in obstetric complications", *J Postgrad Med* 38:183–85 (1992).

Kyte J, and Doolittle RF, "A simple method for displaying the hydropathic character of a protein", *J. Mol. Biol.* 157:105–132 (1982).

Köhler H, and Milstein J, "Continuous cultures of fused cells secreting antibody of predefined specificity", *Nature* 256:495–497 (1975).

Kudryk BJ, Grossman ZD, McAfee JG, and Rosebrough SF, "Monoclonal antibodies as probes for fibrin(ogen) proteolysis", pp. 365–398 in Chatal J–F, ed., *Monoclonal Antibodies in Immunoscintigraphy* CRC Press, Boca Raton, Florida (1989).

Harlow et al., *Cold Spring Harbor Press* Chapters 6, 14 and 15 (1988).

Sevier et al., *Clinical Chemistry* vol. 27 (II) pp. 1797–1806 (1981).

Co, MS et al., *Nature* vol. 351, pp. 501–502 (Jun. 6, 1991).

Weissbach, L. et al., *Proc. Natl. Acad. Sci. USA* 87:5198–5202 (1990).

Fu, Y. et al., Mol. Biol. Cell, 4:75A (1993).

Fu Y. et al., *Thrombosis and Haemostasis* 69 (6): 961 (1993).

Fu, Y et al, Proc. Natl. Acad. Sci., USA, Mar., vol. 91, pp. 2625–2628, 1994.

Fu, Y et al, Biochemistry, vol. 31(48), p. 11968–11972, 1992.

Fu et al, Thrombosis & Haemostasis, vol. 69(6), p. 961, abstract #1513, 1993.

Harlow, E. et al, Chapter 13, pp. 511, 513, 516, 540 and 541., Antibodies, A Laboratory Manuel, 1988.

Kudryk, BJ. et al, Biotechnology, vol. 19, p. 281–313, 1991.

Valenzuela, R et al, Am. J. Pat Nol., vol. 141(4), p. 861–880, 1992.

Weissbach, L. et al, Pro. Nat'l Acad. Sci. USA, vol. 87, Jul., p. 5198–5202, 1990.

Weissbach, L. et al.

FIG-1

```
              620                    640                    660
MAN       DCDDVLQTHPSGTQSGIFNIKLPGSSKIFSVYCDQETSLGGWLLIQQRMDGSLNF NRT WQ
BABOON    ----------------------------------------------------------  ---  --
RABBIT    -------------A--------------------------------------------  ---  --
RAT       -------------A-N---S--------------------------------------  ---  --
CHICKEN   ----IR-K-T--AK----K--PE--N-VL--------T---------------V--  ---  --

680                    700                    720
MAN       DYKRGFGSLNDEGEGEFWLGNDYLHLLTQRGSVLRVELEDWAGNEAYAEYHFRVGSEAEG
BABOON    ----------------------------------------------------Y---------
RABBIT    -----------K----------Q-----L-A---------D-RGD--------------
RAT       -----------K---------------L--------------K----------------
CHICKEN   --R------VDGK-Q--L----ENI-----NDTL--------D--A-----IVQ--T----

740                    760                    780
MAN       YALQVSSYEGTAGDALIEGSVEEGAEYTSHNNMQFSTFDRDADQWEENCAEVYGGGWWYN
BABOON    ----------------------T------S-----------------------------
RABBIT    ------------------------------------------H----------------
RAT       --------Q-------M-------T-----S-----------------------------
CHICKEN   ---T-----------VA-WL---S-----AQ---------Q-H---S------------

800                    820                    840
MAN       NCQAANLNGIYYPGGSYDPR NNS PYEIENGVVWVSFRGADYSLRAVRMKIRPLVTQ
BABOON    --------------------  ---  ---------------------------------
RABBIT    --------------P-----  ---  -----------P-------------.........
RAT       S-------------T-----  ---  --------L--P--------W----------G-
CHICKEN   S-------------H-----  Y-V  ---------IP--AS----KV-------E-L
```

FIG-4

```
             620                  640                  660
RAT     ------------A-N---S------------------------------------
MAN     DCDDVLQTHPSGTQSGIFNIKLPGSSKIFSVYCDQETSLGGWLLIQQRMDGSLNFNRTWQ
RABBIT  ------------A--------------------------------------------

680                  700                  720
RAT     ------------K------------------L--------------K----------
MAN     DYKRG FGSLNDEGEGEFWLG NDYLHLLTQRGSVLRVELEDWAGNEAYAEYHFRVGSEAEG
RABBIT  ------------K----------Q-----L-A----------D-RGD---------

740                  760                  780
RAT     --------Q-------M--------T-----S-------------------------
MAN     YALQVSSYEGTAGDALIEGSVEEGAEYTSHNNMQFSTFDRDADQWEENCAEVYGGGWWYN
RABBIT  -----------------------------------------H----------------

800                  820                  840
RAT     S-------------T--------------L--P---------W----------G-
MAN     NCQAANLNGIYYPGGSYDPRNNSPYEIEN GVVWVSFRGADYSLRAVRMKIRPLVTQ
RABBIT  ---------------P-----------------P------------.........
```

MONOSPECIFIC ANTIBODIES AGAINST A SUBUNIT OF FIBRINOGEN

CROSS REFERENCE TO RELATED APPLICATIONS

This application is a divisional application of copending U.S. application Ser. No. 08/479,755 filed on Jun. 7, 1995, now U.S. Pat. No. 5,817,768.

This invention was made in part with Government support under NIH Grant ROI HL51050 awarded by the Public Health Service. The Government has certain rights in this invention.

BACKGROUND OF THE INVENTION

This invention relates to monospecific antibodies which are reactive with a subclass of fibrinogen. More particularly, the invention relates to monospecific antibodies which are reactive with the $\alpha_E$ subunit of this fibrinogen molecule, and to methods of use of such antibodies.

Fibrinogen is one of the more well-studied and abundant proteins in the human circulatory system. Its complex structure—a heavily disulfide-bonded hexamer composed of two copies each of the $\alpha$, $\beta$ and $\gamma$ subunits—and central role in blood clot formation and wound healing account for the high profile it has enjoyed as a subject of both biochemical and medical research. Recently, new attention has been given to structure/function relationships in the fibrinogen molecule. This new interest has in part been prompted by growth in the understanding of this protein's range of activity in normal and pathological states (Refs. 1–3). However, a major impetus to fibrinogen research has been provided by the recent identification of a long overlooked, naturally occurring variant of the $\alpha$ subunit, designated "$\alpha_E$" (Ref. 4) Unlike the $\alpha$ subunit, the $\alpha_E$ subunit bears a C-terminal extension which confers significant homology to the $\beta$ and $\gamma$ subunits.

Fibrinogen is synthesized and secreted into the circulation by the liver. Circulating fibrinogen is polymerized under attack by thrombin to form fibrin, which is the major component of blood clots or thrombi. Subsequently, fibrin is depolymerized under attack by plasmin to restore the fluidity of the plasma. Many of the steps in the polymerization and depolymerization processes have been well established (Ref. 5). The elevated levels of fibrinogen which are part of the acute phase response occurring in the wake of infections and trauma are now known to come from increased hepatic production, primarily in response to interleukin-6 (IL-6) (Ref. 6).

By the late 1960's, the general subunit structure of fibrinogen was firmly established (Ref. 7) and, a decade later, the complete amino acid sequence was reported (Refs. 8–11). Over the next 10 years, the cluster of three separate genes encoding the $\alpha$ (alpha), $\beta$ (beta), and $\gamma$ (gamma) subunits was identified on chromosome 4q23-q32 (Ref. 12), and the apparently complete genetic sequences of all three fibrinogen subunits were published (Ref. 13). These studies indicated that the $\alpha$ subunit lacked a globular C-terminal domain comparable to those present in the $\beta$ and $\gamma$ subunits.

The subsequent discovery of an additional exon (i.e., exon VI) downstream from the established $\alpha$ subunit gene has resolved the evolutionary mystery posed by the imperfectly parallel structure of the three major subunits (Refs. 4, 14). A novel fibrinogen $\alpha$ chain transcript has been identified at low frequency bearing the exon VI-derived sequences as a separate open reading frame. Additional splicing leads to the use of this extra sequence to elongate the $\alpha$ chain by 35%, providing the subunit with a globular domain (the "VI-domain") similar to those of the $\beta$ and $\gamma$ chains. Evidence shows that this previously unidentified extended $\alpha$ chain ($\alpha_E$) is assembled into fibrinogen molecules and that its synthesis is enhanced by interleukin-6 (IL-6). These facts suggest that the $\alpha_E$ subunit participates in both the acute phase response and in normal physiology.

Using a polyclonal rabbit antibody preparation specific to the VI-domain, $\alpha_E$ was demonstrated to occur in plasma fibrinogen as part of $(\alpha_E \beta \gamma)_2$, a homodimeric (i.e., symmetrical) molecule of ~420 kilodaltons (kDa) (Ref. 15). This species has been designated "$Fib_{420}$" to distinguish it from the abundant 340 kDa form of fibrinogen, denoted "$Fib_{340}$" $((\alpha \beta \gamma)_2)$. Although the relatively low circulating level of $Fib_{420}$ (~1% of total fibrinogen) is undoubtedly responsible for its having escaped detection until recently, the two extra globular domains are likely to significantly influence the fibrinogen molecule's multiple binding capacities and functions.

A definitive topology of the fibrinogen molecule awaits resolution of its elusive crystal structure. However, numerous indirect studies (Ref. 5) point to a trinodal structure, in which the amino ends of all of the chains are contained in a central nodule from which two triple chain disulfide-interlocked coiled coils diverge. These coils lead to two distal nodules made up of the globular, carboxy terminal domains of the $\beta$ and $\gamma$ subunits. Among the more obvious possible functions of the novel globular extension of the $\alpha$ chain C-terminus may be protection of the $\alpha$ chain from proteolytic attack. It is also conceivable that such a domain would alter properties of the protofibrils which constitute the laterally cross-linked fibrin strands, particularly if the domain protruded in a plane distinct from that defined by the other three nodules.

Transcripts encoding fibrinogen subunit counterparts having exceptionally high C-terminal homology to human $\alpha_E$ have been detected thus far in lamprey, where it arises from a second $\alpha$ gene (Refs. 16,17), as well as in chicken, rabbit, rat, and baboon. This degree of $\alpha$ subunit-associated globular domain preservation in the vertebrate genome signals an important, if as yet unknown, role for $\alpha_E$. Clues to the potential significance of variations in the $\alpha$ chain may lie in the similarity of the extension in $\alpha_E$, not only to the corresponding regions of the fibrinogen $\beta$ and $\gamma$ chains, but also to carboxy domains at the C-termini of a number of non-fibrinogen proteins from fruit fly to man (Refs. 18–25). Where functions are known, these non-fibrinogen proteins are constituents of the extracellular matrix and have adhesive properties. It is expected that continued research will permit the determination of whether the $\alpha_E$ globular domain contributes in a subtle way to the primary function of fibrinogen (clot formation and wound healing) or, following the example of other differentially used exons (Refs. 26–28), promotes an alternative function.

In wound repair, fibrinogen serves as a key protein, achieving rapid arrest of bleeding following vessel injury. It promotes both the aggregation of activated platelets with one another to form a hemostatic plug, as well as endothelial cell binding at the site of injury to seal the margins of the wound. As the most abundant adhesive protein in the blood, fibrinogen attaches specifically to platelets, endothelial cells and neutrophils via different integrins (Ref. 29). Five putative receptor recognition domains on human fibrinogen, distributed over its three subunits, have been identified by in vitro and in vivo analyses (Refs. 30–35). In fibrinogen which contains the variant $\alpha_E$ chains, masking of these sites, as well as addition of new sites, are distinct possibilities with ramifications that must be explored. Molecular tools adequate to this purpose have yet to be developed.

Elevated levels of fibrinogen have been found in patients suffering from clinically overt coronary heart disease, stroke and peripheral vascular disease. Although the underlying mechanisms remain speculative, recent epidemiological studies leave little doubt that plasma fibrinogen levels are an independent cardiovascular risk factor possessing predictive power which is at least as high as that of other accepted risk factors such as smoking, hypertension, hyperlipoproteinemia or diabetes (Refs. 36, 37). The structure of fibrin has been analyzed extensively in vitro (Ref. 5). Only recently, however, has attention been paid to the molecular structure of human thrombi and atherosclerotic plaques with respect to fibrinogen and fibrin products (Ref. 38). Whereas thrombi formed in vivo consist primarily of fibrin II cross-linked by factor XIIIa, fibrinogen itself is a major component of uncomplicated atherosclerotic lesions, particularly fibrous and fatty plaques. Immunohistochemical as well as immunoelectrophoretic analyses indicate that fibrinogen in the aortic intima is comparatively well protected from thrombin and plasmin, and that much of it is deposited through direct cross-linking by tissue transglutaminase without becoming converted to fibrin (Ref. 39). Further understanding of these issues awaits the development of methods for the differential determination of fibrinogen subtypes in medical samples.

Fibrinogen-derived protein is also a major component of the stroma in which tumor cells are embedded, but little is known about its molecular structure. Tumor cells promote the secretion of potent permeability factors which cause leakage of fibrinogen from blood vessels (Ref. 3). Extravascular clotting occurs due to procoagulants associated with tumor cells. The resulting fibrinogen/fibrin matrix is constantly remodeled during tumor growth as a consequence of fibrinolysis induced by tumor cell-derived plasminogen activators. It is assumed that fibrin/fibrinogen degradation products play a role during escape of metastatic tumor cells from the primary tumor. There are indications that integrin $\alpha_v\beta_3$, which is known to interact with the RGDS site in the C-terminal region of the $\alpha$ chain, may be an important tumor cell surface receptor since it is preferentially expressed on invasive melanoma (Ref. 40). It is not known what effect the globular domain of $Fib_{420}$'s $\alpha_E$ subunit plays in tumor development.

Despite evidence indicating roles for $\alpha_E$ fibrinogen in a variety of physiological processes, it appears that $\alpha_E$ deficiency is not lethal in man. This inference is drawn from a recent report on fibrinogen Marburg, a homozygous case of dysfibrinogenemia (Ref. 41). In the $\alpha$ gene coding for this abnormal fibrinogen, a single base substitution (A→T) has been identified that changes codon $\alpha$ 461 AAA (lysine) to TAA (stop). As a result, the carboxy-terminal segment 461 to 625 of the common $\alpha$ chain is lacking and no formation of $\alpha_E$ is possible. Symptoms displayed by the homozygous propositus consisted of severe hemorrhage after delivery followed by repeated thrombotic events that occurred, paradoxically, despite unusually low fibrinogen levels. It is not clear whether the mutant $\alpha$ chain itself, or the lack of $\alpha_E$, is responsible for these symptoms.

Fibrinogen levels increase during normal pregnancy (Ref. 42). There is clinical evidence that supports the hypothesis that fibrinogen and firbrin homeostasis is important in pregnancy: low adult levels of (total) fibrinogen were reported to be associated with spontaneous abortions, while fibrinogen infusion was associated with successful gestation (Refs. 43–45). It is undoubtedly significant that, while the fetal concentration of total fibrinogen at term—as measured in umbilical cord blood plasma—is significantly lower than that of adults, the relative level of the $Fib_{420}$ subclass is dramatically (about 10 times) higher. None of these phenomena is understood at the molecular level, bespeaking further need for molecular probes with which to define the role of fibrinogen and its subclasses in the underlying physiological mechanisms.

To this time, no stable, sensitive and precise means has existed for detecting and/or purifying $\alpha_E$-containing fibrinogen ($Fib_{420}$). As noted above, a polyclonal antibody has been generated which exhibits specificity for the $\alpha_E$ subunit (Refs. 4, 15), but such antibodies are notoriously problematic when employed for analytical and diagnostic applications. In particular, polyclonal antibodies by their very nature respond to more than one epitope and, therefore, cannot be used to probe individual subdomains in structure/function analyses of a molecule. Moreover, the specificity of polyclonal antibodies varies from animal to animal, as well as with every immunization, as the various antibody subpopulations fluctuate. Indeed, it is not uncommon that only a single animal can be found which is responsive to an immunogen. These problems prohibit the development of precise, accurate and reproducible methods, tests and diagnostics involving the specific identification of $\alpha_E$ subunit of fibrinogen.

As a result, there exists a need for highly specific, sensitive and reproducible probes for enhancing the understanding of the structure and function of fibrinogen, especially in relation to the $\alpha_E$ subunit thereof. There also exists a need for probes suitable for the detection and purification of the $\alpha_E$ subunit and fibrinogen incorporating the subunit. In addition, means for diagnostic testing of subjects with respect to the amount and distribution of fibrinogen in the body are needed. The present invention effectively addresses these and other needs for the first time.

SUMMARY OF THE INVENTION

The present invention provides monospecific antibodies which are reactive with or bind to single epitopes of the $\alpha_E$ subunit of fibrinogen or a fragment thereof. More particularly, the invention provides monospecific antibodies which are reactive with or bind to different individual epitopes which occur in the globular domain or the VI-domain of the $\alpha_E$ subunit of fibrinogen.

The monospecific antibodies of the invention may include native, modified, or synthetic antibodies. Alternatively, the antibodies may include an antigen-binding region or fragment of a monospecific antibody specific for the $\alpha_E$ subunit. Thus, the invention includes antigen-binding regions such as Fab, F(ab')$_2$, and Fv fragments. The invention further includes chimeric or hybrid antibodies or antigen-binding regions. Such chimeric compounds may include recombinant, synthetic and/or natural fragments of the anti-$\alpha_E$ monospecific antibodies of the invention which have been combined with other antibody or non-antibody substances.

The invention provides further for monospecific antibodies and antigen-binding fragments thereof, as defined elsewhere herein, which are attached through methods known in the art to other moieties such as detectable label moieties and substantially solid substrate materials. For example the invention includes anti-$\alpha_E$ antibodies which have been detectably labeled. Suitable detectable label moieties may be selected from among those known in the art. Substantially solid substrate materials may also be chosen according to the artisan's desired ends.

Further, the invention provides methods for making monospecific antibodies which are specifically reactive with an epitope of the $\alpha_E$ subunit of fibrinogen. Principally, such methods include conventional hybridoma techniques. However, other suitable methods known in the art may be employed, including approaches such as the use of transgenic animals in which fibrinogen genes have been altered or supplemented so as to affect the immune response of the animals to fibrinogen. In addition, recombinant and molecular biology techniques may be employed in the preparation of hybrid antibodies as desired.

The invention also provides a composition for binding fibrinogen, which includes a monospecific antibody or antigen-binding region thereof which is reactive with or binds an epitope of the $\alpha_E$ subunit of fibrinogen or a fragment thereof. The composition may include a pharmacologically acceptable carrier and/or other pharmacologically acceptable components, such as carriers, solvents, salts, excipients, physiological substances, bulking agents, and the like. In addition, the composition may include other components which are separately reactive with fibrinogen, such as other monoclonal or polyclonal antibodies, receptor molecules, or fibrinogen-binding portions thereof. Such compositions may include an anti-$\alpha_E$ monospecific antibody of the invention which has been detectably labeled by a marker moiety. Alternatively, the compositions may also include another fibrinogen-binding component, such as an anti-fibrinogen antibody, which has been detectably labeled by the same or different marker moiety.

The invention further provides a method for binding the $\alpha_E$ subunit of fibrinogen or a fragment thereof by means of an anti-$\alpha_E$ monospecific antibody. Accordingly, $Fib_{420}$ and the $\alpha_E$ subunit, natural, modified, and synthetic variants thereof, as well as fragments thereof, may be detected and measured by means of monospecific antibodies of the invention.

In the fibrinogen binding method of the invention, the method includes contacting a testable system, in which the presence or absence of fibrinogen is to be determined, with a composition having an anti-$\alpha_E$ monospecific antibody or antigen-binding region thereof. The method then involves measuring an amount of specific association or binding between the testable system and the monospecific antibody. In this method, specific binding of the antibody in the system indicates the presence of $\alpha_E$ subunit-containing fibrinogen in the system. The method of the invention may be adapted for performance of numerous immunochemical techniques.

In a preferred embodiment, the detection method employs a monospecific antibody which has been detectably labeled with a marker moiety. In other embodiments, the method may employ a monospecific antibody of the invention which has been bound to a substrate such as a polymeric material. In the method, the composition may also include other reagents such as other antibodies which differentially detect other fibrinogen subunits or subtypes.

Preferred diagnostic methods according to the invention include determining diagnostic iformation associated with atherogenesis and/or thrombogenesis and determining diagnostic information associated with pregnancy status or outcome. Thus in one preferred embodiment, in invention includes a method for diagnosing the presence or probability of thrombogenesis or atherogenesis in a subject, including:

(a) measuring an amount of fibrinogen in a subject by means of a composition comprising a monospecific antibody which binds with an epitope of the $\alpha_E$ subunit of fibrinogen;

(b) comparing the measured amount of fibrinogen for the subject with an amount of fibrinogen recognized to have an association with thrombogenesis or atherogenesis; and (c) determining from the comparison in step (b) the presence or probability of thrombogenesis or atherogenesis in the subject.

In yet another preferred embodiment, the method of the invention includes deriving diagnostic information concerning pregnancy status or outcome, including:

(a) measuring an amount of fibrinogen in a fetal subject by means of a composition comprising a monospecific antibody which binds with an epitope of the $\alpha_E$ subunit of fibrinogen;

(b) comparing the measured amount of fibrinogen for the fetal subject with an amount of fibrinogen recognized to have an association with a pregnancy status or outcome; and (c) determining from the comparison of step (b) information concerning pregnancy status or outcome.

The invention further provides diagnostic and experimental kits which include anti-$\alpha_E$ monospecific antibody, and enable the detection, purification and/or separation of fibrinogen and the various subtypes or fragments thereof in a specific and reproducible manner. In these kits, the antibodies may be provided with means for binding to detectable marker moieties or substrate surfaces. Alternatively, the kits may include the antibodies already bound to marker moieties or substrates.

Accordingly, as a result of the invention, there are now provided monospecific antibodies which are reactive with or bind with epitopes of the VI-domain of the $\alpha_E$ subunit of fibrinogen or a fragment thereof. There are also provided detectable probes for the detection, localization and purification of fibrinogen and specifically the $\alpha_E$ subunit thereof. There are also provided methods for preparing monoclonal antibodies which are reactive with the VI-domain of the $\alpha_E$ subunit of fibrinogen, methods for the preparation of detectable anti-$\alpha_E$ monoclonal antibodies, methods for the use of such antibodies for the detection, localization and purification of $Fib_{420}$ and related compounds, and methods for the diagnosis and treatment of $Fib_{420}$-related disorders.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the present invention. The preferred embodiments of certain aspects of the invention are shown in the accompanying drawings, wherein:

FIG. 1 shows a comparative description of the deduced amino acid sequences of the VI-domain of fibrinogen in five species.

FIG. 4 shows the aligned amino acid sequences of the human, rodent, and rabbit $\alpha_E$ VI-domains

DETAILED DESCRIPTION OF THE INVENTION

Figure 2:
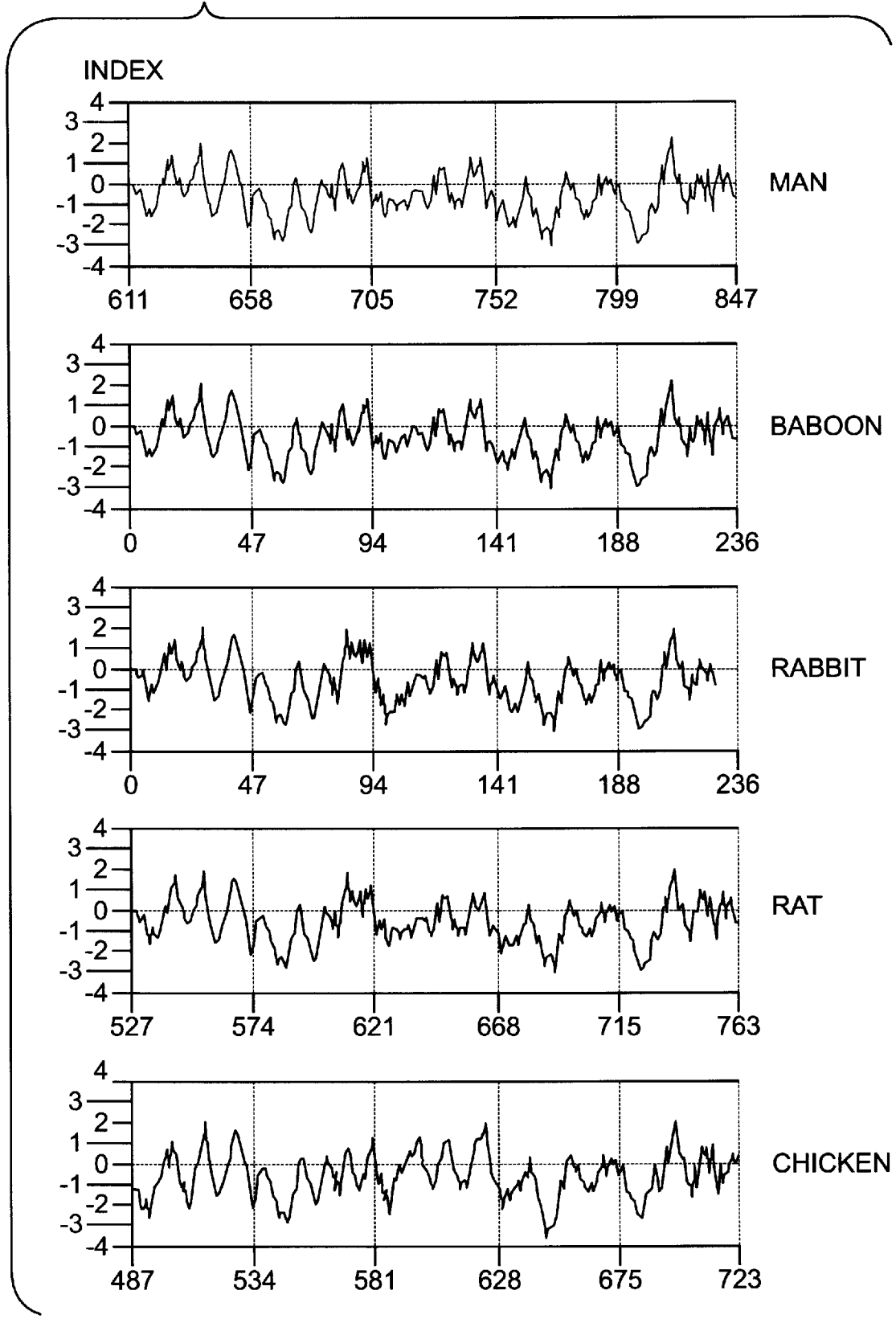
FIG. 2 shows a comparative graphical description of the structure of the VI-domain in five species based on hydropathy analysis of amino acid sequences.

The present invention provides monospecific antibodies which are reactive with or bind with epitopes of the $\alpha_E$ subunit of fibrinogen or a fragment thereof. In particular, the invention provides monospecific antibodies, such as monoclonal antibodies, which are reactive with the VI-domain of the $\alpha_E$ subunit of fibrinogen. The invention also provides compositions containing such monospecific antibodies, as well as detectable probes for the detection, localization and purification of fibrinogen and specifically the $\alpha_E$ subunit thereof. Methods for preparing monoclonal antibodies which are reactive with the VI-domain of the $\alpha_E$ subunit of fibrinogen are also provided. Moreover, methods for the preparation of detectable anti-$\alpha_E$ monoclonal antibodies, methods for the use of such antibodies for the detection, localization and purification of $Fib_{420}$ and related compounds, and methods for the diagnosis and treatment of $Fib_{420}$-related disorders, are also provided.

The monospecific antibodies of the invention may exhibit anti-$\alpha_E$ or anti-VI reactivity which is independent of the molecular or cellular context in which the $\alpha_E$ subunit occurs. Therefore, the invention includes monospecific antibodies which identify epitopes of the $\alpha_E$ subunit or the VI-domain, whether as independent molecules or incorporated into a fibrinogen molecule, whether intracellular or extracellular, or whether naturally occurring (native), modified, or synthetic (e.g., recombinant). The monospecific antibodies of the invention may be specifically reactive with a particular form of $\alpha_E$, or may be reactive with a native or synthetic fragment thereof.

As used herein, the term "monospecific antibody" refers to any homogeneous antibody or antigen-binding region thereof which is reactive with, preferably specifically reactive with, a single epitope or antigenic determinant. The term "monospecific antibody" most commonly refers to a monoclonal antibody, also abbreviated "MoAb", as that term is conventionally understood. The term "monospecific antibody" as used herein may, however, refer to homogeneous antibodies which are native, modified, or synthetic, and can include hybrid or chimeric antibodies. The term does not include "polyclonal antibodies" as that term is commonly understood.

The term "antigen-binding region" refers to a naturally occurring, modified, or synthetic fragment of a monospecific antibody of the invention which is reactive with an epitope of the $\alpha_E$ subunit of fibrinogen. Such antigen-binding regions include, but are not limited to, Fab, F(ab')$_2$, and Fv fragments.

The term "anti-$\alpha_E$" refers to the ability of the monospecific antibodies of the invention to react specifically with $\alpha_E$ fibrinogen or the $\alpha_E$ subunit thereof. Similarly, the term "anti-VI" refers to antibodies of the invention which are specific to or reactive with the VI-domain of $\alpha_E$ fibrinogen.

The term "fibrinogen" without more is intended to include any type of fibrinogen. Fibrinogen, therefore, refers to monomeric and dimeric fibrinogen molecules having the monomer structure $(\alpha\beta\gamma)$, as well as molecules having the monomer structure $(\alpha_E\beta\gamma)$, and other hybrid molecules, whether naturally occurring, modified, or synthetic. The term "fibrinogen" refers generally to fibrinogen from humans but may include fibrinogen of any species. In addition, the term may be specifically limited to a particular species in particular contexts, such as "human fibrinogen".

The term "$Fib_{340}$" refers to the predominant subclass of human fibrinogen, which molecules have the homodimeric structure $(\alpha\beta\gamma)_2$, and have a molecular weight of 340 kilodaltons (kDa) or less. A range of molecular weights of fibrinogen with a maximum of about 340 kDa is normally observed, and is attributed to variations in the lengths of the $\alpha$ subunit tails due to their having been subjected to various amounts of proteolytic cleavage.

The term "$Fib_{420}$" refers to the minor subclass of human fibrinogen, which molecules have the homodimeric structure $(\alpha_E\beta\gamma)_2$, and have a molecular weight of about 420 kDa (Ref. 15). In normal subjects, this type of fibrinogen occurs with a frequency of about 1% of all fibrinogen in the body. This type of fibrinogen generally does not exhibit much variance in molecular weight, probably because the $\alpha$ subunit tail may be substantially protected from random proteolytic attack by virtue of the presence of the additional globular domain peculiar to the $\alpha_E$ subunit.

It is known in the art that monoclonal antibodies are, in general, difficult to produce. For example, it has been estimated that more than 1,000 clones need to be screened to find one or two antibodies which are specific enough and exhibit enough affinity with the antigen to permit use. These difficulties stem from problems such as irreproducibility of an initial positive screen, or failure to obtain subclones in the first cloning. Such problems are commonly related to the deaths of cells, instability in cell lines, low antibody yield in ascites, instability of antibody, etc.

Despite such common difficulties, there have now been produced monospecific antibodies against the $\alpha_E$ subunit of fibrinogen. More particularly, monoclonal antibodies which are reactive with or bind with the VI-domain of the $\alpha_E$ subunit of fibrinogen have been prepared. This achievement was even more unexpected given the further complication that the intended antigen region, i.e., the $\alpha_E$ VI-domain of fibrinogen, is substantially conserved throughout the animal kingdom. It is generally known that the development of monoclonal antibodies is unusually difficult to achieve when the targeted antigenic determinant is part of a highly conserved protein or peptide. This is principally because various related species tend to possess the same or a closely related protein or peptide, and their immune systems perceive such proteins or peptides as "self" antigens. In most cases, an animal of one species will generate little if any immune response when challenged with a highly conserved protein or peptide which is derived from another species. As a result, conserved proteins exhibit little or no immunoreactivity when used to challenge an animal of another species, and the development of antibodies against the protein is correspondingly minimal.

A measure of inter-species homology for the $\alpha_E$ subunit of fibrinogen is illustrated in FIG. 1, in which the amino acid sequence of the human $\alpha_E$ VI-domain is shown in comparison with the corresponding sequences of four other species (baboon, rabbit, rat, and chicken). The deduced amino acid sequences of the $\alpha_E$ VI-domains of man, baboon, rat, rabbit, and chicken align in an uninterrupted block of 236 residues. The complete sequence of amino acids (single letter abbreviations) for the human $\alpha_E$ VI-domain is shown. The dashes (−) in the sequences of the other species indicate residues which exactly match with the corresponding residues in the human sequence, while different amino acid residues are duly indicated by single letter abbreviations.

The human $\alpha_E$ VI-domain (SEQ ID NO:1) shares a striking 99%, 94%, 93%, and 76% amino acid identity, respectively, with its counterparts in baboon (SEQ ID NO:2), rabbit (SEQ ID NO:4), rat (SEQ ID NO:5) and chicken (SEQ ID NO:3). The fact that, in evolutionary terms, at least three quarters of these amino acid positions have remained invariant for 200 million years suggests involvement of the VI-domain in a function vital to the organism.

The VI-domain sequences shown in FIG. 1 were subjected to hydropathy analysis using the parameters given by Kyte and Doolittle (Ref. 46). That the hydropathy plots of the mammalian VI-domains prove to be virtually interchangeable, not only with each other but also with the avian domain (FIG. 2), provides a further indication of the domain's conservation throughout vertebrate evolution.

The skilled artisan will appreciate the extraordinarily high level of homology among these sequences. Moreover, the artisan will further appreciate, a priori, the likely difficulty of raising monoclonal antibodies specifically reactive against the human sequence in an animal of another species. Indeed, the difficulty of generating antibodies of any kind which are free from inter-species cross-reactivity will also be perceived.

In practice, the development of monoclonal antibodies to the VI-domain proved exceptionally difficult. In large part this was due to the high degree of conservation of the VI-domain and its resulting poor immunogenicity. Other complications included the unavailability of purified $Fib_{420}$, requiring cumbersome screening and characterization of MoAbs to the VI-domain. these procedures are detailed elsewhere herein.

Nonetheless, despite these difficulties, the present invention provides hybridoma cell lines which produce monoclonal antibodies reactive with epitopes of the $\alpha_E$ subunit of fibrinogen and fragments thereof. The antibodies produced by these hybridomas are also important aspects of the invention.

The hybridoma technology originally described by Köhler and Milstein (Ref. 47) can be used to prepare hybridoma cell lines whose secretory product, monoclonal antibodies, are reactive with an epitope or antigenic determinant of the $\alpha_E$ subunit of fibrinogen. A general method of preparing these hybridoma cell lines of the invention is described below. Further detail concerning the method is provided in the Examples, which relate the construction of several specific hybridoma cell lines. Those skilled in the art will recognize that the present invention, including the monoclonal antibodies and hybridoma cell lines described in detail herein, provide a variety of ways to make the hybridomas, and thus the antibodies of the invention. The artisan is referred to Kennett et al. (Ref. 48) for further details on hybridoma technology.

Hybridoma cell lines of the invention can be prepared using the $\alpha_E$ subunit of fibrinogen or an immunogenic fragment thereof as immunogenic material for activation of immunologically relevant spleen cells. Spleen cells are then immortalized by fusion with mouse myeloma cells. The hybrid cells, called hybridomas, or hybridoma cell lines resulting from the fusion, are then selected and screened for reactivity with the recombinant VI-domain.

The anti-$\alpha_E$ monospecific antibodies described herein are merely illustrative of the invention, and all monospecific antibodies which are specifically reactive with the $\alpha_E$ subunit or a fragment thereof, regardless of species of origin or immunoglobulin class or subclass designation, including IgG, IgA, IgM, IgE, and IgD, are included in the scope of this invention. The present invention also provides antigen-binding fragments of the anti-$\alpha_E$ antibodies. The ability to bind to the $\alpha_E$ subunit as opposed to non-$\alpha_E$-derived substances (particularly the predominant α subunit) is a general characteristic of monospecific antibodies of the invention.

As discussed above, monospecific antibodies of the invention can be constructed and isolated by immunization, preparation of hybridomas, and identification of antibodies with a reactivity to the $\alpha_E$ subunit of fibrinogen having similarity to that of anti-$\alpha_E$ antibodies described. However, the present invention also provides means for identifying monospecific antibodies of the invention that does not require determination of antibody reactivity with a broad number $\alpha_E$ epitope or fragments. Antibodies of the invention can be identified also by immunoprecipitation and competitive binding studies using the antibody produced by the cell lines described herein.

Immunoprecipitations using the anti-$\alpha_E$ monospecific antibody can be used to determine antigenic identity. Confirmation of identity can be obtained by depleting the antigen from testable samples such as plasma samples, using excess amounts of one anti-$\alpha_E$ antibody and observing the inability of another antibody to immunoprecipitate an $\alpha_E$ fragment from the treated sample. Also, in instances in which the antibodies bind with the same epitope or closely associated epitopes, each antibody will compete with the other(s) for binding to the $\alpha_E$ subunit. Competitive binding studies are generally known in the art.

Treatment of antibody preparations with proteolytic enzymes such as papain and pepsin generates antibody fragments, including the Fab and $F(ab')_2$ species, which retain antigen-binding activity. Treatment of the antibodies of the invention with such enzymes can therefore be used to generate the $\alpha_E$ subunit antigen-binding fragments of the invention. The preparation of antigen-binding fragments of the antibodies of the invention and their diagnostic and therapeutic usefulness, as well as other applications, suggest themselves to the skilled artisan. Antigen-binding fragments of the anti-$\alpha_E$ antibody are especially useful in therapeutic embodiments of the present invention.

Those skilled in the art will recognize that the antigen-binding region of the antibodies and antibody fragments of the invention is a key feature of the present invention. The anti-$\alpha_E$ hybridoma cells of the invention serve as a preferred source of DNA that encodes such antigen-binding regions of the invention. This DNA, through recombinant DNA technology, can be attached to DNA that encodes any desired amino acid residue sequence to yield a novel "hybrid", or "chimeric", DNA sequence that encodes a hybrid, or chimeric, protein. In such a fashion, chimeric antibodies of the invention, in which one portion of the antibody is ultimately derived from one species and another portion of the antibody is derived from another species, can be obtained. However, the present invention also comprises any chimeric molecule that contains an $\alpha_E$ antigen-binding region.

Antibodies of the present invention can also be labeled with any detectable group, such as fluorescent labels, enzyme labels, and radioactive labels to identify expression of the $\alpha_E$ subunit or parts thereof. Detector groups useful according to the invention include, for example, fluorescein as a fluorescent label, horseradish peroxidase as an enzyme label, and Iodine-125 as a radioactive label. Additional fluorescent labels which can be utilized in the invention include, but are not limited to, rhodamine, phycoerythrin and additional compounds emitting fluorescent energy. Additional enzyme labels which can be utilized in this invention include, but are not limited to, glucose oxidase and alkaline phosphatase. Additional radioactive labels which can be utilized in this invention include, but are not limited to, Iodine-131 and Indium-111.

Suitable detectable labels may be selected from among those known in the art, including, but not limited to, radioactive labels, enzymes, specific binding pair components, colloidal dye substances, fluorochromes, reducing substances, latexes, digoxigenin, metals, particulates, dansyl lysine, antibodies, protein A, protein G, electron dense materials, chromophores, and the like. Effectively, any suitable label, whether directly or indirectly detectable, may be employed. One skilled in the art will clearly recognize that these labels set forth above are merely illustrative of the different labels that could be utilized in this invention.

Fibrinogen $\alpha_E$ subunit-reactive antibodies of the invention can also be derivatized by conjugation to biotin, and used, upon addition of species of avidins which have been rendered detectable by conjugation to fluorescent labels, enzyme labels, radioactive labels, electron dense labels, etc., in a multiplicity of immunochemical and immunohistological applications.

The monospecific antibodies of the invention may also be attached or bound to substrate materials according to methods known to those skilled in the art. Such materials are generally substantially solid and relatively insoluble, imparting stability to physical and chemical disruption of the antibodies, and permitting the antibodies to be arranged in specific spatial distributions. Among substrate materials, materials may be chosen according to the artisan's desired ends, and include materials such as gels, hydrogels, resins, beads, nitrocellulose, nylon filters, microtiter plates, culture flasks, polymeric materials, and the like, without limitation.

The monospecific antibodies of the present invention, whether labeled or unlabeled, can be used in immunological assays to determine the presence of $\alpha_E$-containing fibrinogen in tissue samples from human or animal subjects. Biopsy and necropsy samples of subjects, as well as samples from tissue libraries or blood banks, can be evaluated for the presence of $\alpha_E$-containing fibrinogen using an anti-$\alpha_E$ antibody of this invention. Moreover, suitable pharmaceutical preparations according to the invention may be employed for in vivo use, such as for the visualization of fibrinogen or fibrinogen-containing substances and structures in a living subject.

Thus, the invention provides a method for binding the $\alpha_E$ subunit of fibrinogen or a fragment thereof by means of an anti-$\alpha_E$ monospecific antibody. Accordingly, $Fib_{420}$ and the $\alpha_E$ subunit, natural, modified, and synthetic variants thereof, as well as fragments thereof, may be detected and measured by means of monospecific antibodies of the invention.

In the fibrinogen binding method of the invention, the method includes contacting a testable system, in which the presence or absence of fibrinogen is to be determined, with a composition comprising an anti-$\alpha_E$ monospecific antibody or antigen-binding region thereof. The method then involves measuring an amount of specific association or binding between the testable system and the monospecific antibody. In this method, specific binding of the antibody in the system indicates the presence of $\alpha_E$ subunit-containing fibrinogen in the system. The testable system may be either in vivo or in vitro, and the method of the invention may be performed in vivo, in vitro, or a combination thereof.

In a preferred embodiment, the detection method employs a monospecific antibody which has been detectably labeled with a marker moiety. In other embodiments, the method may employ a monospecific antibody of the invention which has been bound to a substrate material. In the method, the composition may also include other reagents such as other antibodies which differentially detect other fibrinogen subunits or subtypes.

The fibrinogen binding method of the invention includes methods known in the art which employ antibodies to specifically bind target substances. Preferred methods include immunochemical methods, such as enzyme-linked immunosorbent assay (ELISA) methods, immunonephelometry methods, agglutination methods, precipitation methods, immunodiffusion methods, immunoelectrophoresis methods, immunofluorescence methods, and radioimmunoassay methods.

The invention further includes a method for determining or diagnosing the existence of or probability of thrombogenesis or atherogenesis in a subject. Alternatively, the method includes the detection and localization of fibrotic or atherosclerotic plaques and/or lesions. In this method, an amount of fibrinogen is measured by means of a composition including an anti-$\alpha_E$ monospecific antibody of the invention. The measured amount of fibrinogen is compared with an amount of fibrinogen which is recognized or known to be associated with thrombogenesis or atherogenesis. The method then involves the determination from the measured and standard value(s) of the presence or likelihood of thrombogenesis or atherogenesis in the subject. The method can include measuring or detecting fibrinogen in vivo, such as by imaging or visualizing the location and/or distribution of fibrinogen, and especially $\alpha_E$ fibrinogen, in the body. Alternatively, the method includes obtaining a medical sample from the subject and measuring fibrinogen ex vivo or in vitro. This method preferably involves the differential measurement of at least two subtypes of fibrinogen, including $\alpha_E$-containing fibrinogen.

The invention also includes a method for fractionation of fibrinogen. Such methods include contacting a medical sample containing fibrinogen with a composition of the invention which includes an anti-$\alpha_E$ monospecific antibody. Preferably, the method is performed using conditions which are conducive to binding of fibrinogen with the monospecific antibody. Then the bound fibrinogen is removed from the sample. The method is represented by chromatography-type methods, both preparative and analytical. Numerous such methods are known in the art and can be selected by the artisan as desired. In this method, the monospecific antibody may be soluble, suspended in fluid phase, or attached to a substantially solid phase, as desired.

The invention further provides diagnostic and experimental kits which include anti-$\alpha_E$ monospecific antibody, and enable the detection, purification and/or separation of fibrinogen and the various subtypes or fragments thereof in a specific and reproducible manner. In these kits, the antibodies may be provided with means for binding to detectable marker moieties or substrate surfaces. Alternatively, the kits may include the antibodies already bound to marker moieties or substrates. The kits may further include positive and/or negative control reagents as well as other reagents for adapting the use of the antibodies of the invention to particular experimental and/or diagnostic techniques as desired. The kits may be prepared for in vivo or in vitro use, and may be particularly adapted for performance of any of the methods of the invention.

The following examples are intended to assist in a further understanding of the invention. The particular materials and conditions employed are intended to be further illustrative of the invention and are not limiting upon the reasonable scope thereof.

EXAMPLE 1

Production and Characterization of Anti-VI MoAbs

Monospecific antibodies (MoAbs) specific for the VI-domain of $\alpha_E$ were sought for their potential use in column-purification of $Fib_{420}$, in immunohistochemical analysis, and in developing an ELISA for measuring the protein in blood samples. Epitope mapping will add these probes to the formidable arsenal of anti-fibrinogen MoAbs, currently available from several sources, to facilitate dissection of $Fib_{420}$'s structure-function relationships.

Recombinant VI-domain was expressed in $E.\ coli$, according to techniques known in the art (Ref. 15). Mice were given subcutaneous injection of either the partial or complete VI-domain amino acid sequence. The partial sequence included 213 amino acids (Gly635-Gln847), and the full sequence included 236 amino acids (Asp612-Gln847). Hybridoma fusions were performed according to standard procedures.

Supernatants of parental clones were initially screened by binding-ELISA (B-ELISA) with recombinant VIdomain. Positive clone supernatnats were then further examined for $\alpha_E$-specificity by B-ELISA with fractionated fibrinogen. Potential $\alpha_E$-specificity was then confirmed by establishing that exclusively the $Fib_{420}$-subclass was immunoprecipitated from metabolically labeled HepG2 culture medium by evaluating the subunit on SDS-PAGE. Western analysis of reduced plasma fibrinogen was then performed to establish that the MoAb did recognize only the $\alpha_E$-subunit of $Fib_{420}$. Only cell populations with supernatants recognizing $\alpha_E$ in native and denatured $Fib_{420}$ by these criteria were subcloned and their MoAbs subtyped. Subclones were amplified as ascites, and the MoAbs were purified by known techniques (E-Z-SEPTM™ antibody purification kit from Pharmacia Biotech (Piscataway, N.J.), as well as size exclusion chromatography and HPLC) from the ascites fluids. The purified MoAbs were then labeled with horseradish peroxidase (HRPO) by known methods. As a result of this screening procedure, three MoAbs were eventually identified which exhibited desirable anti-$\alpha_E$ specificity. These MoAbs were obtained from hybridomas designated #3-10,#29-1,and #148-B.

EXAMPLE 2

Figure 3:
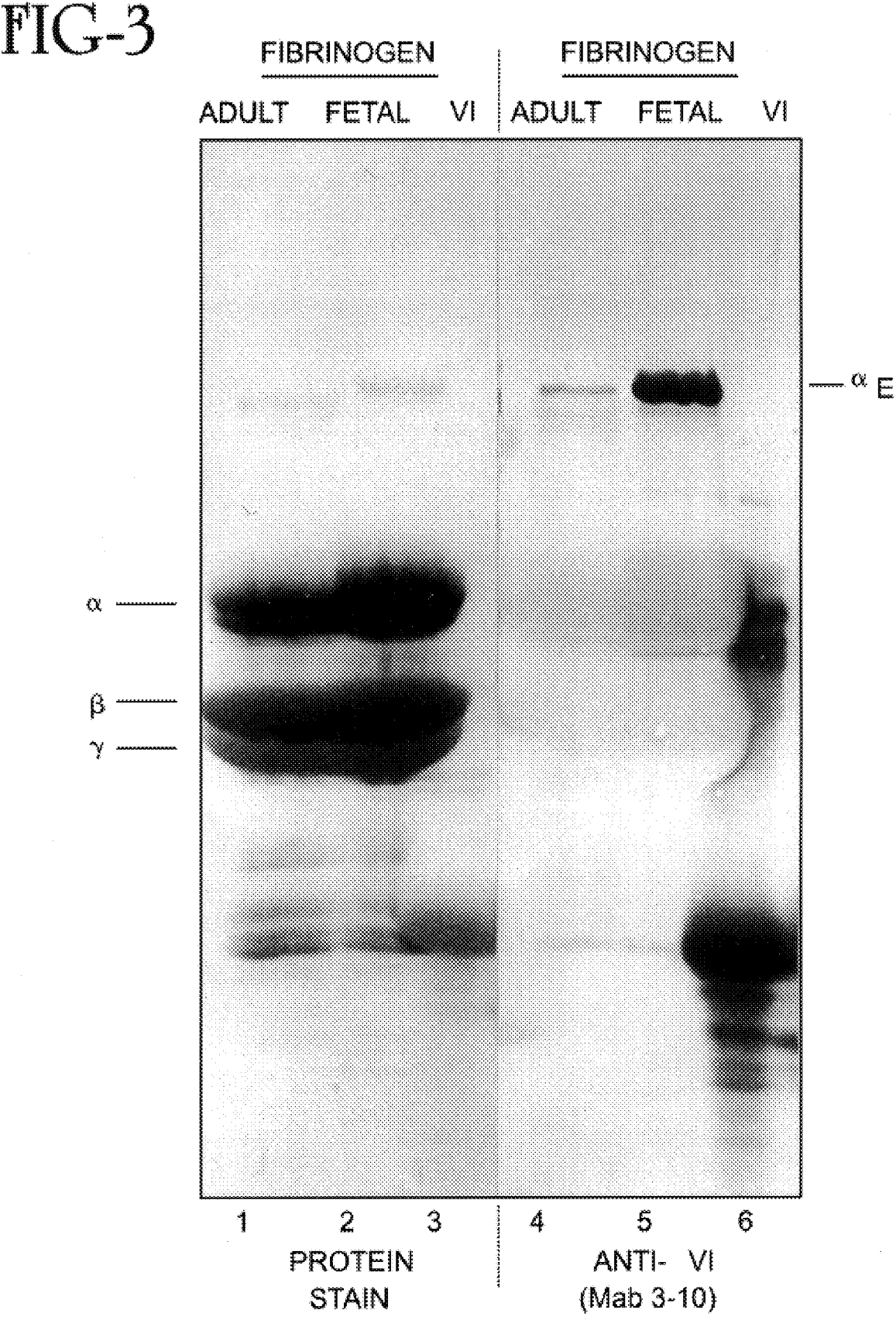
FIG. 3 shows a Western blot analysis of human fibrinogen using anti-$\alpha_E$ antibodies.

A Western analysis using HRPO-labeled MoAb #3-10 is shown in FIG. 3, to illustrate the specificity of the anti-VI MoAbs of the invention. In this analysis, fibrinogen was isolated from normal (adult) plasma, and from umbilical cord (fetal) plasma. Adult (100 μg) and fetal (80 μg) fibrinogen, as well as recombinant VI-domain (25 μg), were separated by PAGE under reducing conditions. In FIG. 3, the adult fibrinogen is shown in Lanes 1 and 4,fetal fibrinogen is shown in Lanes 2 and 4,and recombinant VI-domain is shown in Lanes 3 and 6. Lanes 1–3 are stained for protein, while lanes 4–6 are blotted with MoAb #3-10. It is clear that only $\alpha_E$ is recognized from among all the fibrinogen chains present. These results clearly demonstrate that the invention provides distinct new tools for the immunological detection and analysis of the $\alpha_E$ subunit of fibrinogen.

EXAMPLE 3

To aid in epitope mapping as well as to provide an alternative approach to generating anti-VI MoAbs, we selected several linear sequences of the human VI-domain based both on their immunogenic potential in rodents and rabbits (i.e., significantly different amino acid composition from the aligned sections of these species' $\alpha_E$ C-terminal domains) and on their cell surface location as predicted by hydropathy analysis. Two linear peptides were synthesized according to known techniques. These peptides were designated Region 1 FGSLNDEGEGEFWLG (SEQ ID NO:6) (Phe677-Gly691) and Region 2 GVVWVSFRGADYSL-RAVRMKIRPLVTQ (SEQ ID NO:7) (Gly821-Gln847). The regions are indicated in the shaded portions of FIG. 4 which displays the amino acid sequences of the human, rodent, and rabbit $\alpha_E$ VI-domains. The amino acid sequences were deduced from the human exon VI nucleotide sequences (Ref. 4), and from homologous exon VI sequences of rat and rabbit. Residues identical to the human are indicated by a dash (–). Numbers are provided for the human $\alpha_E$ sequence. The complete rabbit sequence was not determined.

EXAMPLE 4

Use of the synthetic peptides prepared in Example 3 in dot blot analysis and ELISA implicated two epitopes: one near the VI-domain's N-terminus, which is recognized by MoAb #3-10 (Region 1) FGSLNDEGEGEFWLG (SEQ ID NO:6), and one closer to the C-terminus, recognized by MoAbs #29-1 and #148-B (Region 2) GVVWVSFRGADYSL-RAVRMKIRPLVTQ (SEQ ID NO:7).

Figure 5:
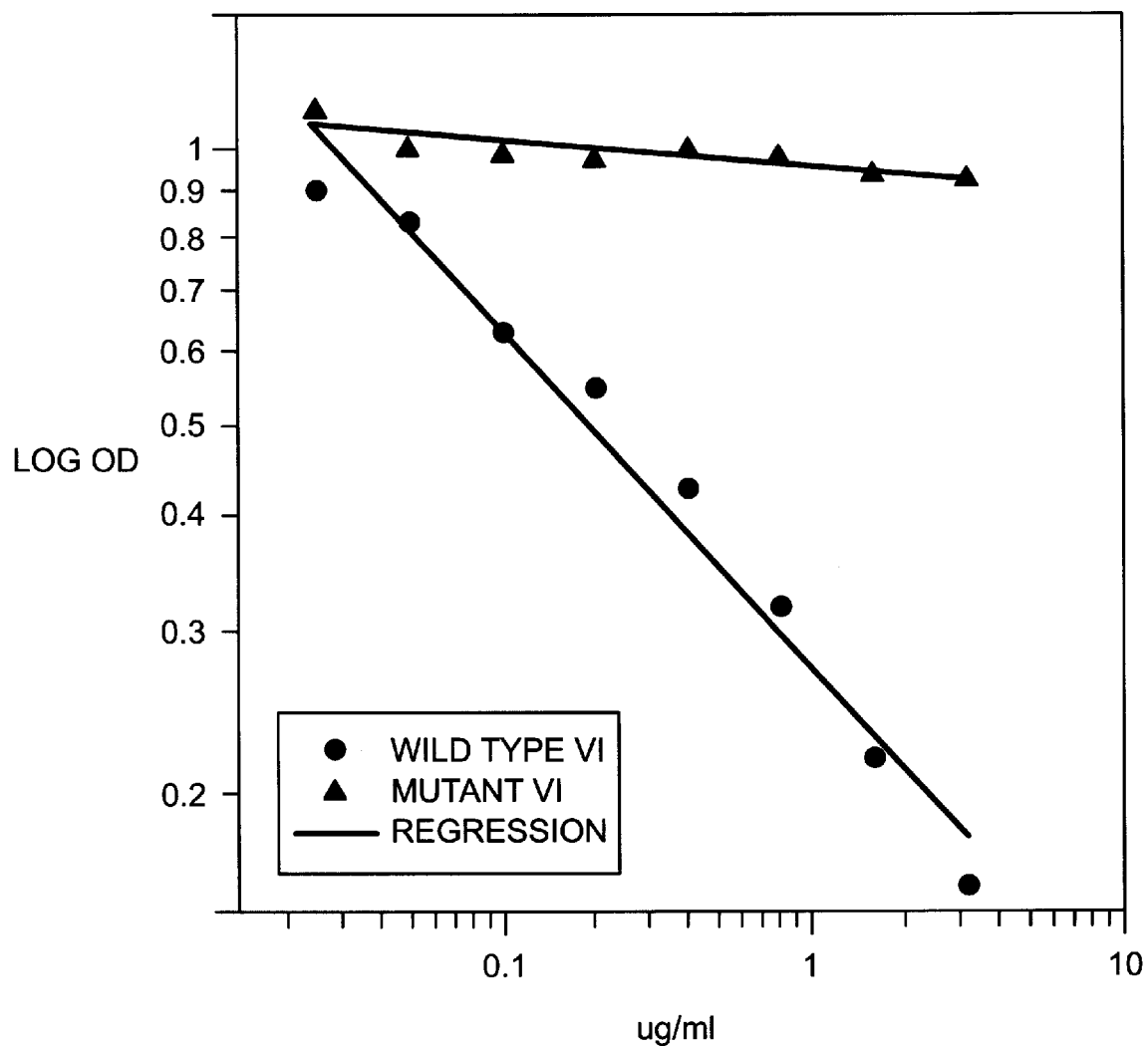
FIG. 5 shows a plot of competition-ELISA using an anti-$\alpha_E$ antibody of the invention with wild-type and mutant recombinant human VI-domains as competitors.

The specificity of these assays, which require notoriously high molar concentrations of the small synthetic peptides, was verified using point mutations and truncations of the VI-domain that were generated and expressed in $E.\ coli$ according to methods known in the art. FIG. 5 shows that mutation of Region 1 of the $\alpha_E$-VI-domain (i.e., 683 E→K, in imitation of the rodent sequence) renders the mutant ineffective as a competitor in C-ELISA with MoAb #3-10. With MoAb #29-1,by contrast, wild-type and mutant domains were found to be equally potent (data not shown). The results confirm Region 1 of the VI-domain as including the epitope recognized by #3-10.

EXAMPLE 5

Figure 6A:
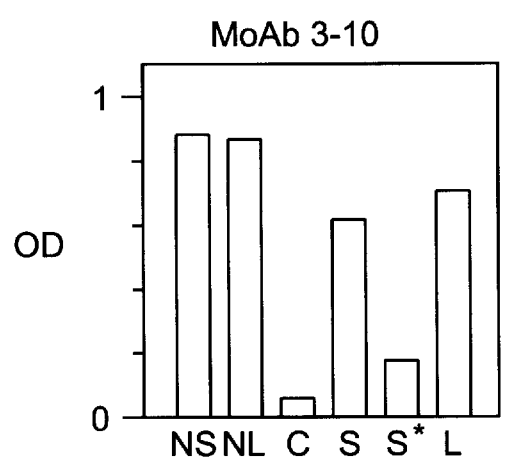
FIGS. 6(a)–6(c) are bar graphs showing binding-ELISA of wild-type, truncated, and mutated recombinant VI-domains (the latter expressed in *E. coli*) using monospecific anti-$\alpha_E$ antibodies of the invention.
Figure 6B:
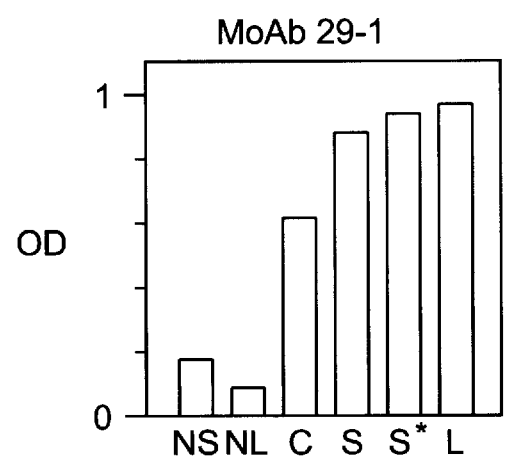
Figure 6C:
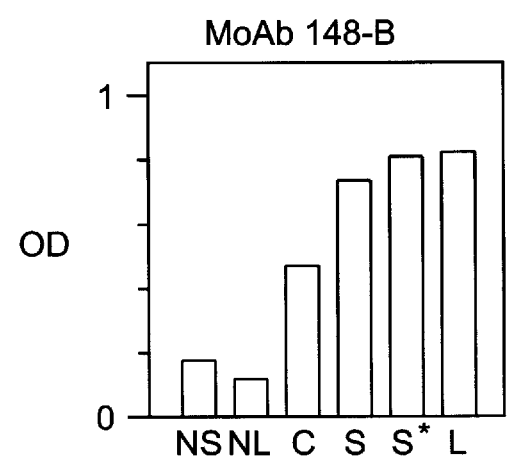

Binding-ELISA (B-ELISA) assays using truncations of the VI-domain (FIGS. 6(a)–(c)) corroborated and extended the findings shown in Example 4 to suggest the sites recognized by the other two MoAbs. Microtiter wells were coated with different recombinant VI-domains as indicated on the abscissa of each panel. "S" indicates the "short", partial VI-domain (residues 635–847); "L" indicates the "long", complete VI-domain (residues 612–847); "S*" indicates the S partial VI-domain which had been mutated in Region 1 (683 E→K); the prefix "N" indicates the N-terminal half of the domain (terminating with residue 717); and "C" represents their common C-terminal halves (beginning with residue 717).

FIG. 6(a) shows that MoAb #3-10 bound significantly only to N-terminal segments that include an intact region 1

(NS and NL), but not to a C-terminal segment (C) nor to the region 1-mutant (S*). Conversely, MoAbs #29-1 (FIG. 6(b)) and #148-B (FIG. 6(c)) failed to bind the N-terminal segments (NS and NL), but do bind both the C-terminal segment (C) and the mutant (S*). The latter observation supports the notion that the epitope for MoAbs #29-1 and #148-B lies in the C-terminal region. All of the MoAbs identified the short (S) and long (L) domains, as expected.

EXAMPLE 6

To separate $Fib_{420}$ from $Fib_{340}$, a one-step procedure using ion-exchange chromatography has yielded two fibrinogen fractions. Commercially available fibrinogen preparations (available from, e.g., Sigma Chemical Co., St Louis, Mo., and American Diagnostica, Greenwich, Conn.) were fractionated by DEAE-cellulose chromatography. Western blots were used to characterize each fraction with regard to the presence of $Fib_{420}$. One fraction, Fraction A, was found to contain no $Fib_{420}$. In the other fraction, Fraction B, $Fib_{420}$ was found to constitute 10–15% of the protein (about 50% of this fraction is fibrinogen).

Figure 7:
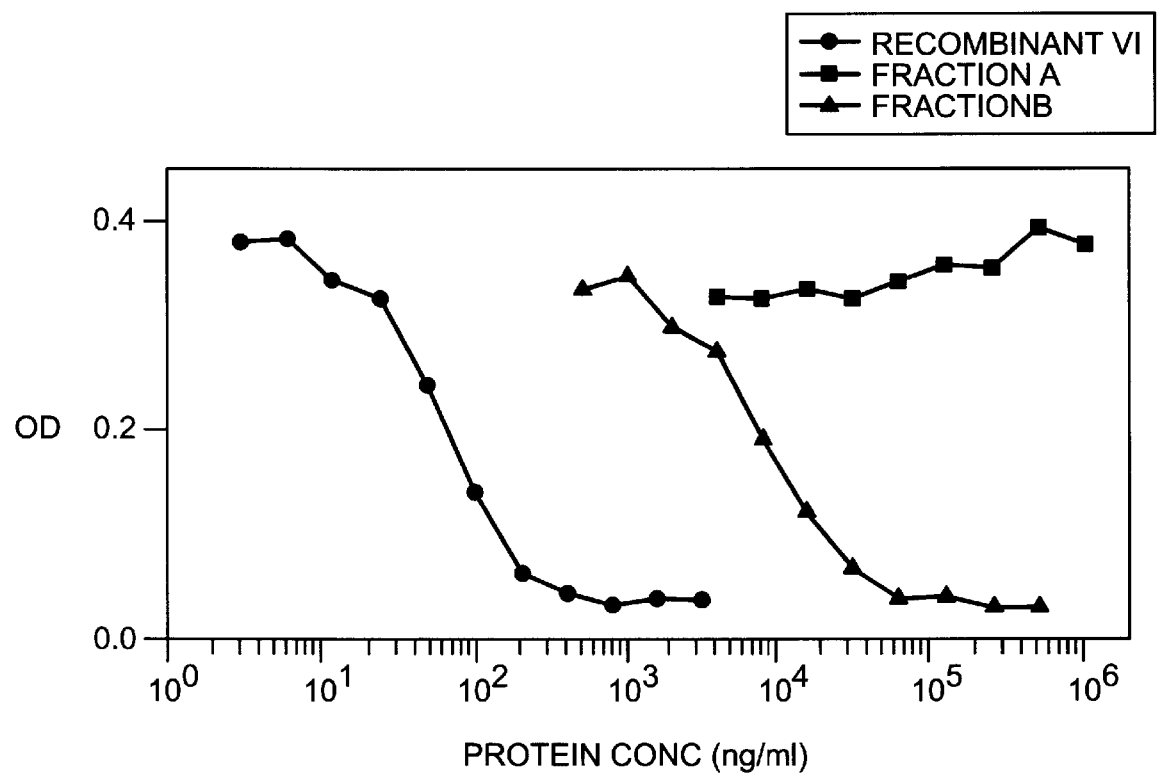
FIG. 7 shows competition-ELISA with recombinant VI-domain, and fraction A- and fraction B-fibrinogen as competitors using MoAb #3-10.

The competitive strength of Fractions A and B in C-ELISA was compared to that of the recombinant VI-domain. FIG. 7 is a plot illustrating the C-ELISA data. It is shown that Fraction A was not reactive in this system, whereas Fraction B shows typical concentration-dependent competition. Recombinant VI-domain was approximately 100-fold more reactive than Fraction A. The C-ELISA data are, therefore, consistent with the Western blot observations for Fractions A and B.

EXAMPLE 7

Identification of the Glycosylation Site of $\alpha_E$

In contrast to the predominant human α chain which has no carbohydrate, human $\alpha_E$ is N-glycosylated (Ref. 15). Of the two potential glycosylation sites in its VI-domain, the tripeptide at Asn667 is conserved in all vertebrates (including lamprey), while the second, at Asn812, is conserved only in mammals (FIG. 1). By mutation of these sites (As→Gln) using conventional techniques, we found that COS cells attach carbohydrate only to Asn667 and that this conserved site is also critical for proper $Fib_{420}$ assembly and secretion.

EXAMPLE 8

Recombinant $\alpha_E$-fibrinogen and its Subdomains

Recombinant $Fib_{420}$ as well as its subdomains may be generated by methods known in the art, preferably in yeast such as *Saccharomyces cerevisiae*, and *Pichia pastoris*. Using the Pichia system, our laboratory has succeeded in expressing soluble VI-domains which appear to be glycosylated. It should be noted that solubilization of the non-glycosylated bacterial recombinant VI-domain was achieved only after denaturation with urea. It is believed that the soluble recombinant domain from yeast folds similarly to the domain in native $Fib_{420}$. This material can serve as an antigen for developing a new generation of MoAbs that are capable of recognizing alternative (also non-linear) epitopes and/or are better suited to immunopurification of native $Fib_{420}$ from plasma. The soluble wild-type domain and its mutants are also extremely important as probes with which to examine the participation of $Fib_{420}$ in polymerization and cross-linking and to define the molecule's suspected role as ligand of integrins and other receptors involved in cell-cell and cell-matrix interactions.

EXAMPLE 9

Figure 8:
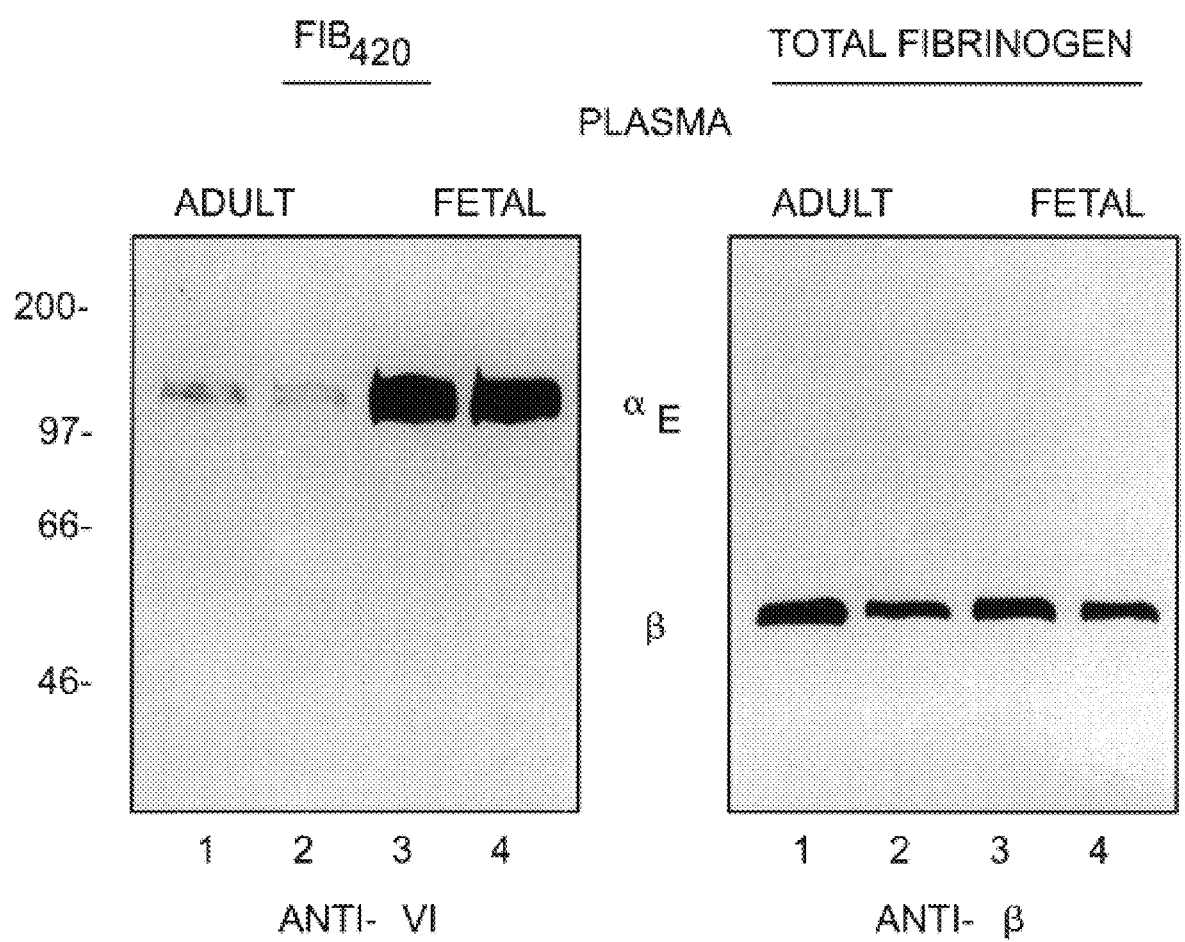
FIG. 8 shows a Western blot analysis of adult and fetal fibrinogen levels by means of a monospecific antibody of the invention.

Human and fetal fibrinogen was analyzed by Western blot, using the MoAb 3-10 according to the invention. Plasma samples, prepared according to standard procedures from CPDA-1 adult blood and umbilical cord blood, were subjected to electrophoresis under reducing conditions. Four representative samples of adult and fetal plasma are shown in FIG. 8, with the amount of total fibrinogen being approximately equal in each lane. $Fib_{420}$ and total fibrinogen levels were determined by measuring $\alpha_E$ and β subunits by Western analysis using anti-VI (MoAb 3-10) or anti-β (MoAb Ea3 (Ref. 49)), respectively. The left panel of FIG. 8 illustrates $Fib_{420}$ (1 μL adult plasma; 3 μL fetal plasma), and the right panel illustrates total fibrinogen (10 nL adult plasma; 30 nL fetal plasma). FIG. 7 shows that $Fib_{420}$ is present as a much larger (approximately 10 times) proportion of fibrinogen in fetal plasma than in adult plasma.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

REFERENCES

1. Blomback B, "Fibrinogen and fibrin formation and its role in fibrinolysis", in Goldstein J, ed., *Biotechnology of Blood*, 225–279 (1991).
2. Bini A, and Kudryk B J, "Fibrin and its derivatives in the normal and diseased vessel wall", *Ann. N.Y. Acad. Sci.* 667:112–126 (1992).
3. Dvorak H F, Nagy J A, Berse B, Brown L F, Yeo K-T, Yeo T-K, Dvorak A M, Van de Water L, Sioussat TM, and Senger D R, "Vascular Permeability factor, fibrin, and the pathogenesis of tumor stroma formation", *Ann N.Y. Acad. Sci.* 667:101–111 (1992).
4. Fu Y, Weissbach L, Plant P W, Oddoux C, Cao Y, Liang T J, Roy S N, Redman C M, and Grieninger G, "Carboxy-terminal-extended variant of the human fibrinogen α subunit: a novel exon conferring marked homology to β and γ subunits", *Biochemistry* 31:11968–11972 (1992).
5. Doolittle R F, "Fibrinogen and fibrin", *Annu. Rev. Biochem.* 53:195–229 (1984).
6. Sehgal P B, Grieninger G, and Tosato G, eds., "Regulation of the acute phase and immune responses: Interleukin-6", *Ann. N.Y. Acad. Sci.* 557:1–583 (1989).
7. Blomback B, Blomback M, Henschen A, Hessel B, Iwanaga S, and Woods K R, "N-terminal disulphide knot of human fibrinogen", *Nature* 218: 130–134 (1968).
8. Lottspeich F, and Henschen A, "Amino acid sequence of human fibrin. Preliminary note on the completion of the gamma-chain sequence", *Hoppe-Seyler's Z. Physiol. Chem.* 358:935–938 (1977).
9. Henschen A, and Lottspeich F, "Amino Acid sequence of human fibrin, preliminary note on the completion of the beta-chain sequence", *Hoppe-Sevler's Z. Physiol. Chem.* 358:1643–1646 (1977).
10. Henschen A, Lottspeich F, and Hessel B, "Amino acid sequence of human fibrin, preliminary note on the completion of the intermediate part of the alpha-chain sequence", *Hoppe-Seyler's Z. Physiol. Chem.* 360:1951–1956 (1979).
11. Doolittle R F, Watt K W K, Cottrell B A, Strong D D, and Riley M, "The amino acid sequence of the alpha-chain of human fibrinogen", *Nature* 280:464–468 (1979).
12. Kant J A, Fornace Jr A J, Saxe D, Simon M I, McBride O W, and Crabtree G R, "Evolution and organization of the fibrinogen locus on chromosome 4: Gene duplication accompanied by transposition and inversion", *Proc. Natl. Acad. Sci. USA* 82:2344–2348 (1985).

13. Chung D W, Harris J E, and Davie E W, "Nucleotide sequences of the three genes coding for human fibrinogen", *Adv. Exp. Med. Biol.* 281:39–48 (1991).
14. Weissbach L, and Grieninger G, "Bipartite mRNA for chicken alpha-fibrinogen potentially encodes an amino acid sequence homologous to beta- and gamma-fibrinogens", *Proc. Natl. Acad. Sci. USA* 87:5198–5202 (1990).
15. Fu Y, and Grieninger G, "$Fib_{420}$: A normal human variant of fibrinogen with two extended α chains", *Proc. Natl. Acad. Sci. USA* 91:2625–2628 (1994).
16. Pan Y, and Doolittle R F, "cDNA sequence of a second fibrinogen alpha chain in lamprey: An archetypal version alignable with full-length beta and gamma chains", *Proc. Natl. Acad. Sci. USA* 89:2066–2070 (1992).
17. Doolittle R F, Riley M, and Pan Y, "Direct measurement of a second fibrinogen alpha chain in lamprey blood plasma", *Thromb. Res.* 68:489–493 (1992)
18. Chung D W, Que B G, Rixon M W, Mace Jr M, and Davie E W, "Characterization of complementary deoxyribonucleic acid and genomic deoxyribonucleic acid for the beta chain of human fibrinogen", *Biochemistry* 22:3244–3250 (1983).
19. Chung D W, Chan W-Y, and Davie E W, "Characterization of a complementary deoxyribonucleic acid coding for the gamma chain of human fibrinogen", *Biochemistry* 22:3250–3256 (1983).
20. Baker N E, Mlodzik M, and Rubin G M, "Spacing differentiation in the developing Drosophila eye: A fibrinogen-related lateral inhibitor encoded by scabrous", *Science* 250:1370–1377 (1990).
21. Koyama T, Hall L R, Haser W G, Tonegawa S, and Saito H, "Structure of a cytotoxic T-lymphocyte-specific gene shows a strong homology to fibrinogen beta and gamma chains", *Proc. Natl. Acad. Sci. USA* 84:1609–1613 (1987).
22. Morel Y, Bristow J, Gitelman S E, and Miller W L, "Transcript encoded on the opposite strand of the human steroid 21-hydroxylase/complement component C4 gene locus", *Proc. Natl. Acad. Sci. USA* 86:6582–6586 (1989).
23. Nies D E, Hemesath T J, Kim J-H, Gulcher J R, and Stefansson K, "The complete cDNA sequence of human hexabreachion (tenascin)", *J. Biol. Chem.* 266:2818–2823 (1991).
24. Norenberg U, Wille H, Wolff J M, Frank R, and Rathjen F G, "The chicken neural extracellular matrix molecule restrictin: Similarity with EGF-, fibronectin type III-, and fibrinogen-like motifs", *Neuron* 8:849–863 (1992).
25. Xu X, and Doolittle R F, "Presence of a vertebrate fibrinogen-like sequence in an echinoderm", *Proc. Natl. Acad. Sci. USA* 87:2097–2101 (1990).
26. Chan AM-L, Rubin J S, Bottaro D P, Hirschfield D W, Chedid M, and Aaronson S A, "Identification of a competitive HGF antagonist encoded by an alternative transcript", *Science* 254:1382–1385 (1991).
27. Descombes P, and Schibler U, "A liver-enriched transcriptional activator protein, LAP, and a transcriptional inhibitory protein, LIP, are translated from the same mRNA", *Cell* 67:569–579 (1991).
28. Early P, Rogers J, David M, Calame K, Bond M, Wall R, and Hood L, "Two mRNAs can be produced from a single immunoglobulin mu gene by alternative RNA processing pathways", *Cell* 20:313–319 (1980).
29. Hynes R O, "Integrins: Versatility, modulation, and signaling in cell adhesion", *Cell* 69:11–25 (1992).
30. Kloczewiak M, Timmons S, Lukas T J, and Hawiger J, "Platelet receptor recognition site on human fibrinogen. Synthesis and structure-function relationship of peptides corresponding to the carboxy-terminal segment of the gamma chain", *Biochemistry* 23:1767–1774 (1984).
31. Cheresh D A, Berliner S A, Vicente V, and Ruggeri Z M, "Recognition of distinct adhesive sites on fibrinogen by related integrins on platelets and endothelial cells", *Cell* 58:945–953 (1989).
32. Loike J D, Sodeik B, Cao L, Leucona S, Weitz J I, Detmers P A, Wright S D, and Silverstein SC, "CD11c/CD18 on neutrophils recognizes a domain at the N terminus of the A-alpha chain of fibrinogen", *Proc. Natl. Acad. Sci. USA* 88:1044–1048 (1991).
33. Farrell D H, Thiagarajan P, Chung D W, and Davie E W, "Role of fibrinogen alpha and gamma chain sites in platelet aggregation", *Proc. Natl. Acad. Sci. USA* 89:10729–10732 (1992).
34. Gonda S R, and Shainoff J R, "Adsorptive endocytosis of fibrin monomer by macrophages: Evidence of a receptor for the amino terminus of the fibrin alpha chain", *Proc. Natl. Acad. Sci. USA* 79:4565–4569 (1982).
35. Ribes J A, Ni F, Wagner D D, and Francis C W, "Mediation of fibrin-induced release of von Willebrand factor from cultured endothelial cells by the fibrin beta chain", *J. Clin Invest.* 84:435–442 (1989).
36. Ernst E, "Plasma fibrinogen—An independent cardiovascular risk factor", *J. Internal Med.* 227:365–372 (1990).
37. Ernst E, and Resch K L, "Fibrinogen as a cardiovascular risk factor: A meta-analysis and review of the literature", *Ann Intern. Med.* 118:956–963 (1993).
38. Bini A, Fenoglio J J, Sobel J, Owen J, Fejgl M, and Kaplan K L, "Immunochemical characterization of fibrinogen, fibrin I, and fibrin II in human thrombi and atherosclerotic lesions", *Blood* 69:1038–1045 (1987).
39. Valenzuela R, Shainoff J R, DiBello P M, Urbanic D A, Anderson J M, Matsueda G R, and Kudryk B J, "Immunoelectrophoretic and immunohistochemical characterizations of fibrinogen derivatives in atherosclerotic aortic intimas and vascular prosthesis pseudo-intimas", *Am. J. Pathol.* 141:861–880 (1992).
40. Felding-Habermann B, Ruggeri Z M, and Cheresh D A, "Distinct biological consequences of integrin alpha-v-beta-3-mediated melanoma cell adhesion to fibrinogen and its plasmic fragments", *J. Biol. Chem.* 267:5070–5077 (1992).
41. Koopman J, Haverkate F, Grimbergen J, Egbring R, and Lord S T, "Fibrinogen Marburg: A homozygous case of dysfibrinogenemia, lacking amino acids A-alpha 461–610 (Lys 461 AAA—Stop TAA)", *Blood* 80:1972–1979 (1992).
42. Justus B, Siegert G, and Tiebel O,"Changes of parameters of hemostasis and fibrinolysis during normal pregnancy", *Zent bl Gynäkol* 114:165–70 (1992) (in German).
43. Kitchens C S, Cruz A C, and Kant J A, "A unique 7p/12q chromosomal abnormality associated with recurrent abortion and hypofibrinogenemia", *Blood* 70:921–25 (1987).
44. Goodwin T M, "Congenital hypofibrinogenemia in pregnancy", *Obstet Gynecol* 44:157–61 (1989).
45. Parasnis H, Raje B, and Hinduja I N, "Relevance of plasma fibrinogen estimation in obstetric complications", *J Postgrad Med* 38:183–85 (1992).
46. Kyte J, and Doolittle R F, "A simple method for displaying the hydropathic character of a protein", *J. Mol. Biol.* 157:105–132 (1982).

47. Köhler H, and Milstein J, "Continuous cultures of fused cells secreting antibody of predefined specificity", *Nature* 256:495–497 (1975).
48. Kennett R H, McKearn T J, and Bechtol K B, eds., *Monoclonal Antibodies: Hybridomas: A New Dimension in Biological Analyses*, Plenum Press, New York (1980).
49. Kudryk B J, Grossman Z D, McAfee J G, and Rosebrough S F, "Monoclonal antibodies as probes for fibrin (ogen) proteolysis", pp. 365–398 in Chatal J-F, ed., *Monoclonal Antibodies in Immunoscintigraphy* CRC Press, Boca Raton, Fla. (1989).

What is claimed is:

1. A method of detecting fibrinogen which comprises:

(1) contacting a testable system with an isolated monospecific antibody which specifically binds with the peptide consisting of FGSLNDEGEGEFWLG (SEQ ID NO:6) or GVVWVSFRGADYSLRAVRMKIRPLVTQ (SEQ ID NO:7); and (2) measuring specific binding of said monospecific antibody to said peptide in the testable system, wherein specific binding of the monospecific antibody in said testable system is associated with the presence of fibrinogen, and wherein said testable system is an in vivo testable system.

2. A method for purifying fibrinogen, comprising:

contacting a sample containing fibrinogen with a composition comprising a monospecific antibody produced by a hybridoma cell line selected from the group consisting of hybridoma cell line #3-10, hybridoma cell line #29- 1, and hybridoma cell line #148-B, said monospecific antibody specifically binds with the $\alpha_E$ subunit of fibrinogen, under conditions conducive to binding of fibrinogen with said monospecific antibody, and selectively removing fibrinogen bound to said monospecific antibody from said sample.

3. The method of claim 2, wherein said monospecific antibody is soluble.

4. The method of claim 2, wherein said monospecific antibody is suspended in a fluid phase.

5. The method of claim 2, wherein said monspecific antibody is attached to a solid phase.

6. A method for purifying fibrinogen, comprising:

contacting a sample containing fibrinogen with an isolated monospecific antibody which specifically binds with the peptide consisting of FGSLNDEGEGEFWLG (SEQ ID NO:6) or GVVWVSFRGADYSL-RAVRMKIRPLVTQ (SEQ ID NO:7) of the $\alpha_E$ subunit of fibrinogen, under conditions conducive to binding of fibrinogen with said monospecific antibody, and selectively removing fibrinogen bound to said monospecific antibody from said sample.

7. The method of claim 6, wherein said monospecific antibody is soluble.

8. The method of claim 6, wherein said monospecific antibody is suspended in a fluid phase.

9. The method of claim 6, wherein said monspecific antibody is attached to a solid phase.

* * * * *

SEQUENCE LISTING

<160> NUMBER OF SEQ ID NOS: 7

<210> SEQ ID NO 1
<211> LENGTH: 236
<212> TYPE: PRT
<213> ORGANISM: Homo sapiens

<400> SEQUENCE: 1

```
Asp Cys Asp Asp Val Leu Gln Thr His Pro Ser Gly Thr Gln Ser Gly
 1               5                  10                  15

Ile Phe Asn Ile Lys Leu Pro Gly Ser Ser Lys Ile Phe Ser Val Tyr
            20                  25                  30

Cys Asp Gln Glu Thr Ser Leu Gly Gly Trp Leu Leu Ile Gln Gln Arg
        35                  40                  45

Met Asp Gly Ser Leu Asn Phe Asn Arg Thr Trp Gln Asp Tyr Lys Arg
    50                  55                  60

Gly Phe Gly Ser Leu Asn Asp Glu Gly Glu Gly Phe Trp Leu Gly
 65                  70                  75                  80

Asn Asp Tyr Leu His Leu Leu Thr Gln Arg Gly Ser Val Leu Arg Val
                85                  90                  95

Glu Leu Glu Asp Trp Ala Gly Asn Glu Ala Tyr Ala Glu Tyr His Phe
            100                 105                 110

Arg Val Gly Ser Glu Ala Glu Gly Tyr Ala Leu Gln Val Ser Ser Tyr
        115                 120                 125

Glu Gly Thr Ala Gly Asp Ala Leu Ile Glu Gly Ser Val Glu Glu Gly
    130                 135                 140

Ala Glu Tyr Thr Ser His Asn Asn Met Gln Phe Ser Thr Phe Asp Arg
145                 150                 155                 160

Asp Ala Asp Gln Trp Glu Glu Asn Cys Ala Glu Val Tyr Gly Gly Gly
                165                 170                 175

Trp Trp Tyr Asn Asn Cys Gln Ala Ala Asn Leu Asn Gly Ile Tyr Tyr
            180                 185                 190

Pro Gly Gly Ser Tyr Asp Pro Arg Asn Asn Ser Pro Tyr Glu Ile Glu
        195                 200                 205

Asn Gly Val Val Trp Val Ser Phe Arg Gly Ala Asp Tyr Ser Leu Arg
    210                 215                 220

Ala Val Arg Met Lys Ile Arg Pro Leu Val Thr Gln
225                 230                 235
```

<210> SEQ ID NO 2
<211> LENGTH: 236
<212> TYPE: PRT
<213> ORGANISM: PAPIO SP.

<400> SEQUENCE: 2

```
Asp Cys Asp Asp Val Leu Gln Thr His Pro Ser Gly Thr Gln Ser Gly
 1               5                  10                  15

Ile Phe Asn Ile Lys Leu Pro Gly Ser Ser Lys Ile Phe Ser Val Tyr
            20                  25                  30
```

```
Cys Asp Gln Glu Thr Ser Leu Gly Gly Trp Leu Leu Ile Gln Gln Arg
        35                  40                  45

Met Asp Gly Ser Leu Asn Phe Asn Arg Thr Trp Gln Asp Tyr Lys Arg
 50                  55                  60

Gly Phe Gly Ser Leu Asn Asp Glu Gly Glu Gly Phe Trp Leu Gly
 65                  70                  75                  80

Asn Asp Tyr Leu His Leu Leu Thr Gln Arg Gly Ser Val Leu Arg Val
                85                  90                  95

Glu Leu Glu Asp Trp Ala Gly Asn Glu Ala Tyr Ala Glu Tyr Tyr Phe
                100                 105                 110

Arg Val Gly Ser Glu Ala Glu Gly Tyr Ala Leu Gln Val Ser Ser Tyr
            115                 120                 125

Glu Gly Thr Ala Gly Asp Ala Leu Ile Glu Gly Ser Val Glu Glu Gly
    130                 135                 140

Thr Glu Tyr Thr Ser His Asn Ser Met Gln Phe Ser Thr Phe Asp Arg
145                 150                 155                 160

Asp Ala Asp Gln Trp Glu Glu Asn Cys Ala Glu Val Tyr Gly Gly Gly
                165                 170                 175

Trp Trp Tyr Asn Asn Cys Gln Ala Ala Asn Leu Asn Gly Ile Tyr Tyr
                180                 185                 190

Pro Gly Gly Ser Tyr Asp Pro Arg Asn Asn Ser Pro Tyr Glu Ile Glu
            195                 200                 205

Asn Gly Val Val Trp Val Ser Phe Arg Gly Ala Asp Tyr Ser Leu Arg
        210                 215                 220

Ala Val Arg Met Lys Ile Arg Pro Leu Val Thr Gln
225                 230                 235

<210> SEQ ID NO 3
<211> LENGTH: 236
<212> TYPE: PRT
<213> ORGANISM: GALLUS SP.

<400> SEQUENCE: 3

Asp Cys Asp Asp Ile Arg Gln Lys His Thr Ser Gly Ala Lys Ser Gly
  1               5                  10                  15

Ile Phe Lys Ile Lys Pro Glu Gly Ser Asn Lys Val Leu Ser Val Tyr
                20                  25                  30

Cys Asp Gln Glu Thr Thr Leu Gly Gly Trp Leu Leu Ile Gln Gln Arg
        35                  40                  45

Met Asp Gly Ser Val Asn Phe Asn Arg Thr Trp Gln Asp Tyr Arg Arg
 50                  55                  60

Gly Phe Gly Ser Val Asp Gly Lys Gly Gln Gly Glu Leu Trp Leu Gly
 65                  70                  75                  80

Asn Glu Asn Ile His Leu Leu Thr Gln Asn Asp Thr Leu Leu Arg Tyr
                85                  90                  95

Glu Leu Glu Asp Trp Asp Gly Asn Ala Ala Tyr Ala Glu Tyr Ile Val
                100                 105                 110

Gln Val Gly Thr Glu Ala Glu Gly Tyr Ala Leu Thr Val Ser Ser Tyr
            115                 120                 125

Glu Gly Thr Ala Gly Asp Ala Leu Val Ala Gly Trp Leu Glu Glu Gly
    130                 135                 140

Ser Glu Tyr Thr Ser His Ala Gln Met Gln Phe Ser Thr Phe Asp Arg
145                 150                 155                 160

Asp Gln Asp His Trp Glu Glu Ser Cys Ala Glu Val Tyr Gly Gly Gly
```

-continued

```
                    165                 170                 175
Trp Trp Tyr Asn Ser Cys Gln Ala Ala Asn Leu Asn Gly Ile Tyr Tyr
                180                 185                 190

Pro Gly Gly His Tyr Asp Pro Arg Tyr Asn Val Pro Tyr Glu Ile Glu
            195                 200                 205

Asn Gly Val Val Trp Ile Pro Phe Arg Ala Ser Asp Tyr Ser Leu Lys
        210                 215                 220

Val Val Arg Met Lys Ile Arg Pro Leu Glu Thr Leu
225                 230                 235

<210> SEQ ID NO 4
<211> LENGTH: 236
<212> TYPE: PRT
<213> ORGANISM: LEPORIDAE SP.

<400> SEQUENCE: 4

Asp Cys Asp Asp Val Leu Gln Thr His Pro Ser Gly Ala Gln Ser Gly
  1               5                  10                  15

Ile Phe Asn Ile Lys Leu Pro Gly Ser Ser Lys Ile Phe Ser Val Tyr
             20                  25                  30

Cys Asp Gln Glu Thr Ser Leu Gly Gly Trp Leu Leu Ile Gln Gln Arg
         35                  40                  45

Met Asp Gly Ser Leu Asn Phe Asn Arg Thr Trp Gln Asp Tyr Lys Arg
     50                  55                  60

Gly Phe Gly Ser Leu Asn Asp Lys Gly Glu Gly Glu Phe Trp Leu Gly
 65                  70                  75                  80

Asn Asp Gln Leu His Leu Leu Thr Leu Arg Ala Ser Val Leu Arg Val
                 85                  90                  95

Glu Leu Glu Asp Trp Asp Gly Arg Gly Asp Tyr Ala Glu Tyr His Phe
            100                 105                 110

Arg Val Gly Ser Glu Ala Glu Gly Tyr Ala Leu Gln Val Ser Ser Tyr
        115                 120                 125

Glu Gly Thr Ala Gly Asp Ala Leu Ile Glu Gly Ser Val Glu Glu Gly
    130                 135                 140

Ala Glu Tyr Thr Ser His Asn Asn Met Gln Phe Ser Thr Phe Asp Arg
145                 150                 155                 160

Asp Ala Asp His Trp Glu Glu Asn Cys Ala Glu Val Tyr Gly Gly Gly
                165                 170                 175

Trp Trp Tyr Asn Asn Cys Gln Ala Ala Asn Leu Asn Gly Ile Tyr Tyr
            180                 185                 190

Pro Gly Gly Pro Tyr Asp Pro Arg Asn Asn Ser Pro Tyr Glu Ile Glu
        195                 200                 205

Asn Gly Val Val Trp Val Pro Phe Arg Gly Ala Asp Tyr Ser Leu Arg
    210                 215                 220

Ala Val Arg Met Lys Ile Arg Pro Leu Val Thr Gln
225                 230                 235

<210> SEQ ID NO 5
<211> LENGTH: 236
<212> TYPE: PRT
<213> ORGANISM: RATTUS SP.

<400> SEQUENCE: 5

Asp Cys Asp Asp Val Leu Gln Thr His Pro Ser Gly Ala Gln Asn Gly
  1               5                  10                  15

Ile Phe Ser Ile Lys Leu Pro Gly Ser Ser Lys Ile Phe Ser Val Tyr
```

```
                    20                  25                   30
Cys Asp Gln Glu Thr Ser Leu Gly Gly Trp Leu Leu Ile Gln Gln Arg
            35                  40                  45

Met Asp Gly Ser Leu Asn Phe Asn Arg Thr Trp Gln Asp Tyr Lys Arg
 50                  55                  60

Gly Phe Gly Ser Leu Asn Asp Lys Gly Glu Gly Glu Phe Trp Leu Gly
 65                  70                  75                  80

Asn Asp Tyr Leu His Leu Leu Thr Leu Arg Gly Ser Val Leu Arg Val
                85                  90                  95

Glu Leu Glu Asp Trp Ala Gly Lys Glu Ala Tyr Ala Glu Tyr His Phe
            100                 105                 110

Arg Val Gly Ser Glu Ala Glu Gly Tyr Ala Leu Gln Val Ser Ser Tyr
            115                 120                 125

Gln Gly Thr Ala Gly Asp Ala Leu Met Glu Gly Ser Val Glu Glu Gly
            130                 135                 140

Thr Glu Tyr Thr Ser His Ser Asn Met Gln Phe Ser Thr Phe Asp Arg
145                 150                 155                 160

Asp Ala Asp Gln Trp Glu Glu Asn Cys Ala Glu Val Tyr Gly Gly Gly
                165                 170                 175

Trp Trp Tyr Asn Ser Cys Gln Ala Ala Asn Leu Asn Gly Ile Tyr Tyr
                180                 185                 190

Pro Gly Gly Thr Tyr Asp Pro Arg Asn Asn Ser Pro Tyr Glu Ile Glu
            195                 200                 205

Asn Gly Val Leu Trp Val Pro Phe Arg Gly Ala Asp Tyr Ser Leu Trp
    210                 215                 220

Ala Val Arg Met Lys Ile Arg Pro Leu Val Gly Gln
225                 230                 235

<210> SEQ ID NO 6
<211> LENGTH: 15
<212> TYPE: PRT
<213> ORGANISM: Homo sapiens

<400> SEQUENCE: 6

Phe Gly Ser Leu Asn Asp Glu Gly Glu Gly Glu Phe Trp Leu Gly
 1               5                  10                  15

<210> SEQ ID NO 7
<211> LENGTH: 27
<212> TYPE: PRT
<213> ORGANISM: Homo sapiens

<400> SEQUENCE: 7

Gly Val Val Trp Val Ser Phe Arg Gly Ala Asp Tyr Ser Leu Arg Ala
 1               5                  10                  15

Val Arg Met Lys Ile Arg Pro Leu Val Thr Gln
                20                  25
```